(12) United States Patent
August et al.

(10) Patent No.: US 8,318,173 B2
(45) Date of Patent: Nov. 27, 2012

(54) CHIMERIC VACCINES

(75) Inventors: Thomas August, Baltimore, MD (US); Ernesto Marques, Jr., Baltimore, MD (US)

(73) Assignee: The John Hopkins University, Baltimore, MD (US)

( * ) Notice: Subject to any disclaimer, the term of this patent is extended or adjusted under 35 U.S.C. 154(b) by 1329 days.

(21) Appl. No.: 10/474,371

(22) PCT Filed: Apr. 5, 2002

(86) PCT No.: PCT/US02/10757
§ 371 (c)(1),
(2), (4) Date: Mar. 5, 2004

(87) PCT Pub. No.: WO02/080851
PCT Pub. Date: Oct. 17, 2002

(65) Prior Publication Data
US 2004/0157307 A1  Aug. 12, 2004

Related U.S. Application Data

(60) Provisional application No. 60/281,607, filed on Apr. 5, 2001, provisional application No. 60/281,608, filed on Apr. 5, 2001, provisional application No. 60/281,621, filed on Apr. 5, 2001.

(51) Int. Cl.
*C07K 16/00* (2006.01)
*C12P 21/08* (2006.01)
*A61K 39/00* (2006.01)

(52) U.S. Cl. ............. 424/185.1; 424/192.1; 530/388.73; 530/388.75

(58) Field of Classification Search .................. None
See application file for complete search history.

(56) References Cited

FOREIGN PATENT DOCUMENTS
WO    WO 94/17192    8/1994

OTHER PUBLICATIONS

Ruff et al. The enhanced immune response to the HIV gp160/LAMP chimeric gene product targeted to the lysosome membrane protein trafficking pathway. The Jouranl of Biological Chemistry Mar. 28, 1997, vol. 272, No. 13, p. 8671-8678.*
Juuti-Uusitalo et al. Selective targeting of avidin/mannose 6-phosphate receptor chimeras to early or late endosomes. European Journal of Cell Biology Jul. 2000, vol. 79, No. 7, p. 458-468. Abstract only provided.*
Simmen et al. The tyrosinase tail mediates sorting to the lysosomal compartment in MDCK cells via a di-leucine and a tyrosine-based signal. Journal of Cell Science 1999, vol. 112, p. 45-53.*
Mathews et al. The Pathway and Targeting Signal for Delivery of the Integral Membrane Glycoprotein LEP100 to Lysosomes. The Journal of Cell Biology, vol. 118, No. 5, pp. 1027-1040.*
Conibear et al. A chimera of the cytoplasmic tail of the mannose 6-phosphate/IGF-II receptor and lysozyme localizes to the TGN rather than prelysosomes where the bulk of the endogenous receptor is found. Journal of Cell Science 1994, vol. 107, pp. 923-932.*
Rosshart et al. The Cytoplasmic Domain Mediates Localization of Furin to the trans-Golgi Network En Route to the Endosomal/Lysosomal System. The Journal of Cell Biology 1994, vol. 126, No. 5, 1157-1172.*
Danilczyk et al. Functional Relationship between Calreticulin, Calnexin, and the Endoplasmic Reticulum Luminal Domain of Calnexin. The Journal of Biological Chemistry 2000, vol. 275, No. 17, pp. 13089-13097.*
Nishino et al. Primary LAMP-2 deficiency causes X-linked vacuolar cardiomyopathy and myopathy (Danon disease). Nature 2000, vol. 406, p. 901-910.*
Pakula et al. Genetic Analysis of Protein Stability and Function. Annual Reviews of Genetics 1989, vol. 23, pp. 289-310.*
Oestreicher et al. A Single Amino Acid Change in a Pathway-Specific Transcription Factor Results in Differing Degrees of Constitutivity, Hyperinducibility and Derepression of Several Structural Genes. Journal of Molecular Biology 1995, vol. 249, p. 693-699.*
Hunziker et al. Intracellular trafficking of lysosomal membrane proteins. BioEssays 1996, vol. 18, No. 5, pp. 379-389.*
Wu. T.C. et al, Engineering an intracellular pathway for major histocompatibility complex class II presentation of antigens, PNAS, Dec. 1995, vol. 92, pp. 11671-11675.
Smahel. M. et al. Modified HPV16 E7 Genes as DNA Vaccine against E7-Containing Oncogenic Cells, Virology, Mar. 2001, vol. 281, pp. 231-238.
Wu, et al., "Engineering an Intracellular Pathway for Major Histocompatibility Complex Class II Presentation of Antigens," Proc. Natl. Acad. Sci. USA, vol. 92, pp. 11671-11675, 1995.

* cited by examiner

*Primary Examiner* — Louise Humphrey
(74) *Attorney, Agent, or Firm* — Edwards Wildman Palmer LLP; Peter F. Corless; Andrew W. Shyjan, Esq.

(57) ABSTRACT

The invention provides chimeric proteins and nucleic acids encoding these which can be used to generate vaccines against selected antigens. In one aspect, a chimeric protein comprises an antigen sequence and a domain for trafficking the protein to an endosomal compartment, irrespective of whether the antigen is derived from a membrane or non-membrane protein. In one preferred aspect, the trafficking domain comprises a lumenal domain of a LAMP polypeptide. Alternatively, or additionally, the chimeric protein comprises a trafficking domain of an endocytic receptor (e.g., such as DEC-205 or gp200-MR6). The vaccines (DNA, RNA or protein) can be used to modulate or enhance an immune response against any kind of antigen. In one preferred aspect, the invention provides a method for treating a patient with cancer by providing a chimeric protein comprising a cancer-specific antigen or a nucleic acid encoding the protein to the patient.

13 Claims, 12 Drawing Sheets

Fig. 1: A) Schematic representation of the different plasmid constructs. B) Western blot analysis of COS cells transfected with different plasmids probed with anti-Gag).
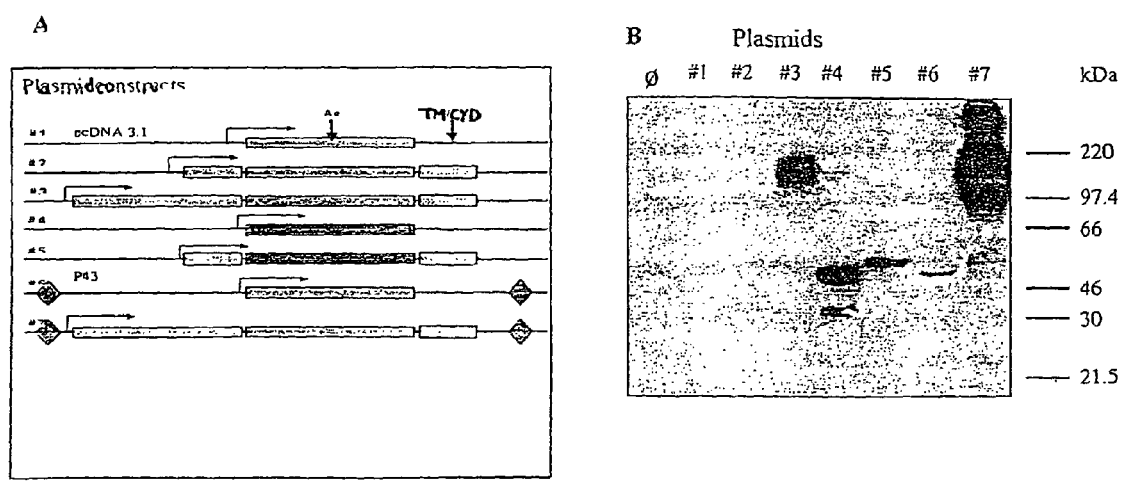

Figure 2. Anti-HIV lysate antibody response, average of individual mice (n=5).
ELISA analysis of antibody binding to protein of an HIV-1 viral triton-X-100 lysate, 50 ul of 5 ug/ml added to plate
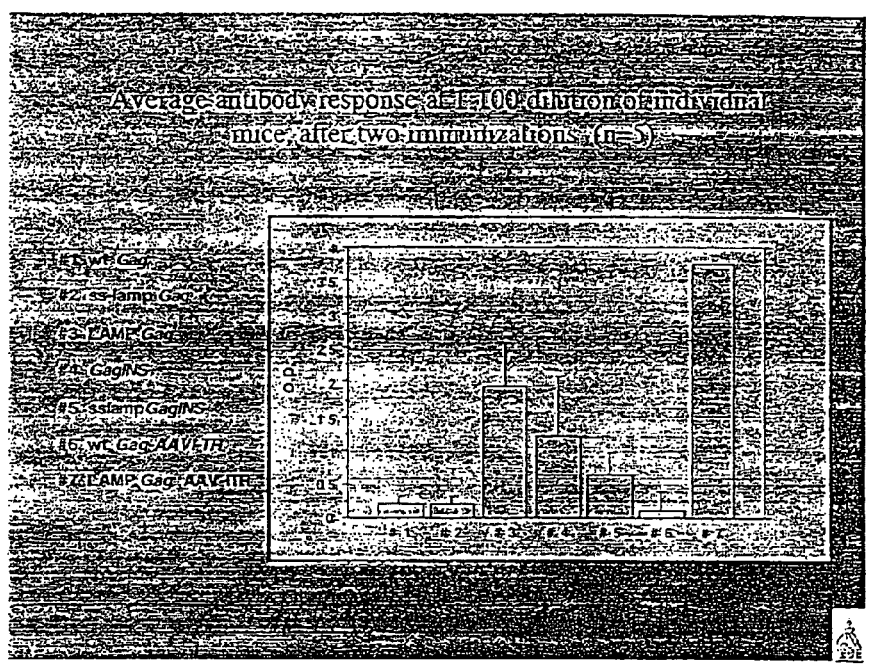

Figure 3 Titer of anti-HIV lysate antibody response, individual immunizations.
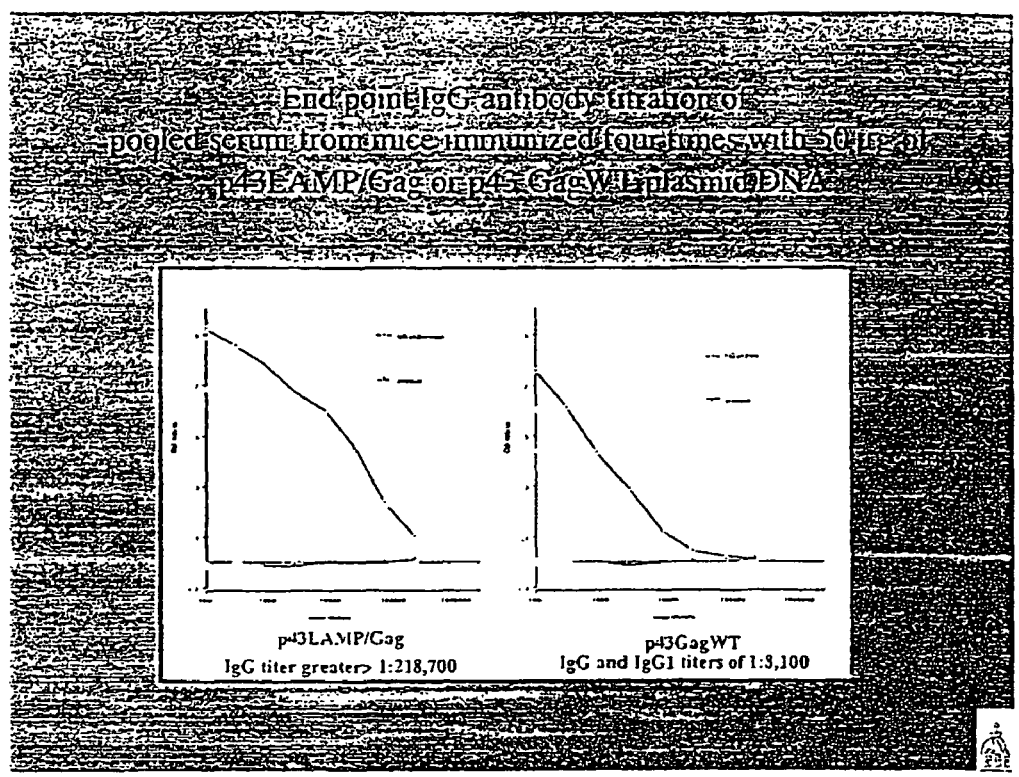

FIGURES 4A-B  Anti-HIV lysate antibody response at day 29 after the first immunization and 15 days after the second immunization; average of individual mice (n=6).
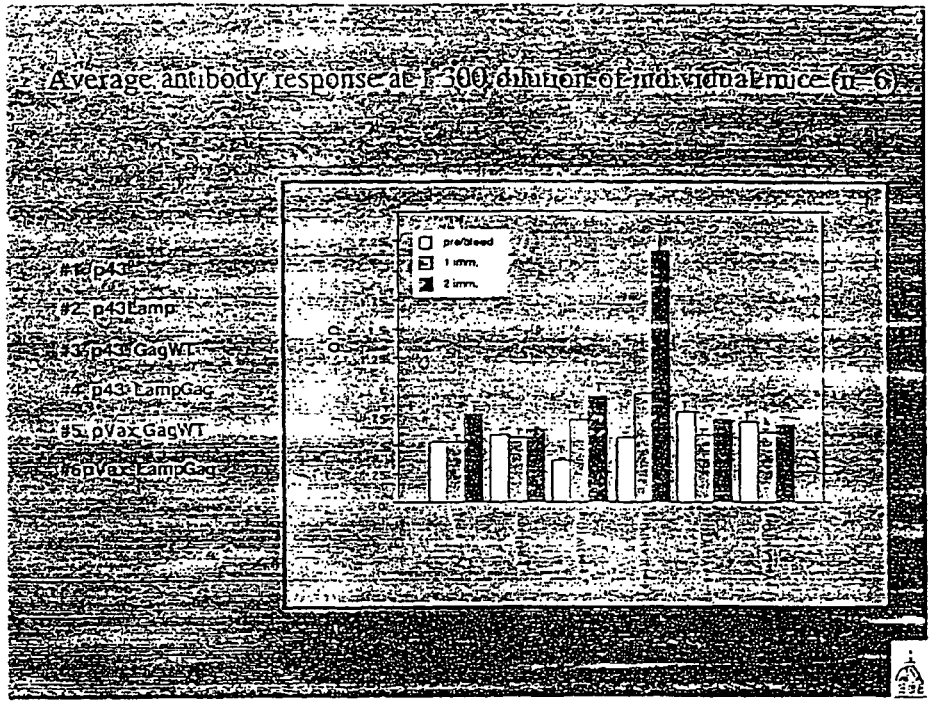
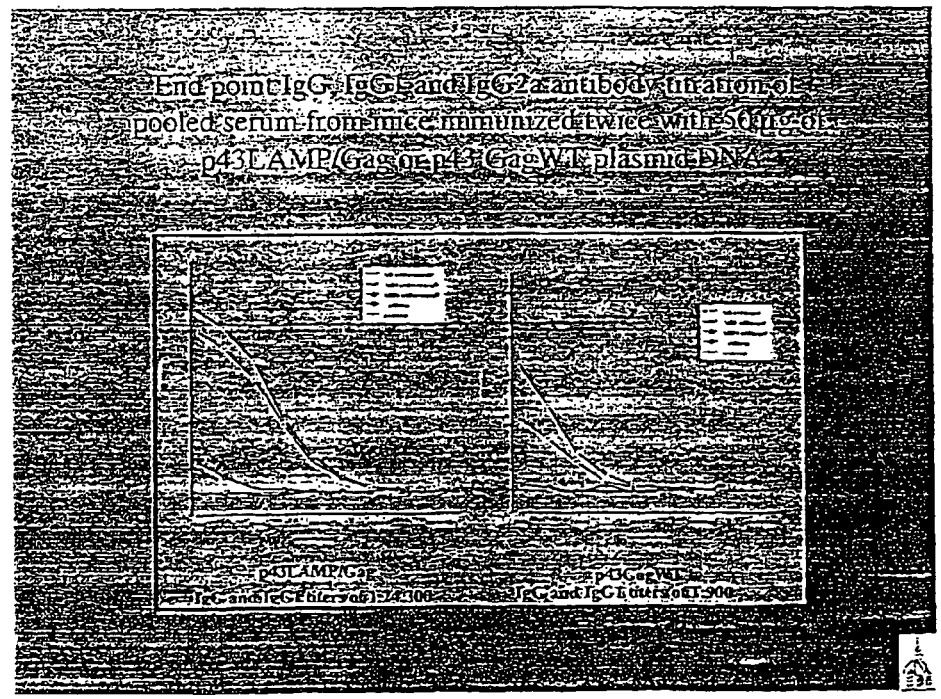

Fig. 5  Interferon gamma and IL4 assay at day 45 after immunization with 50 ug DNA on days 0 and 30. Spleen cells were stimulated by medium (control), 5 µg Gag protein, LEFT: p55 Gag protein specific IL4 production.
RIGHT: p55 Gag-specific INFγ production
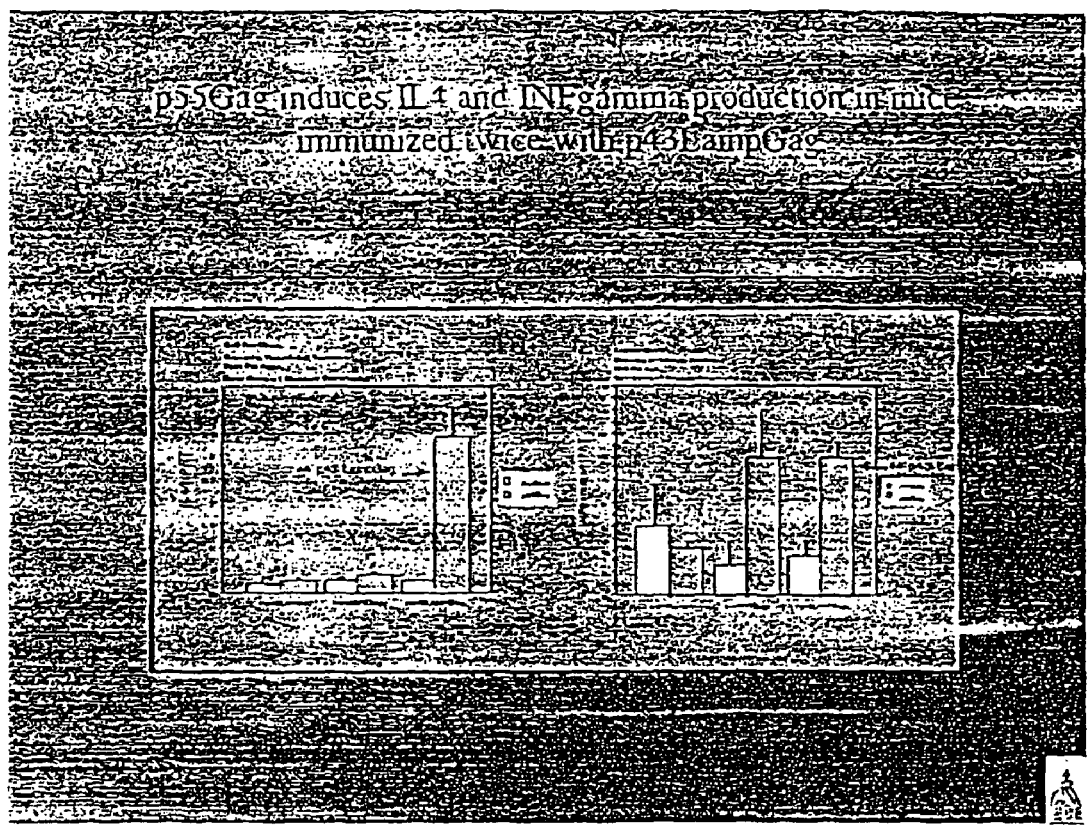

LEFT: p55 Gag protein specific IL4 production.
RIGHT: p55 Gag-specific INFγ production
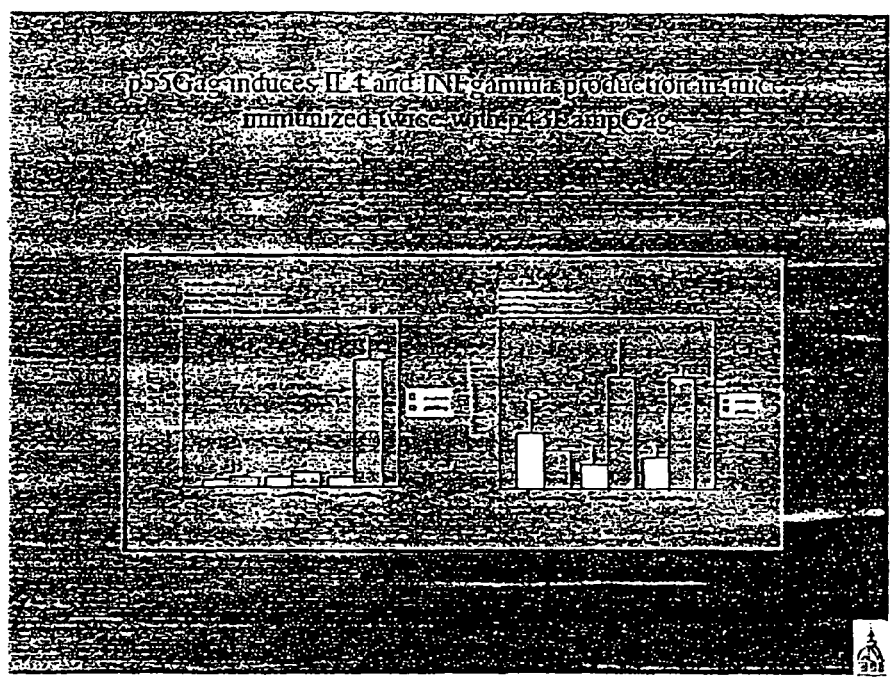
Fig. 6  IL-4 real time PCR assay at day 45 after immunization with 50 ug DNA on days 0 and 30. Spleen cells were stimulated by medium (control), and 5 μg Gag protein.

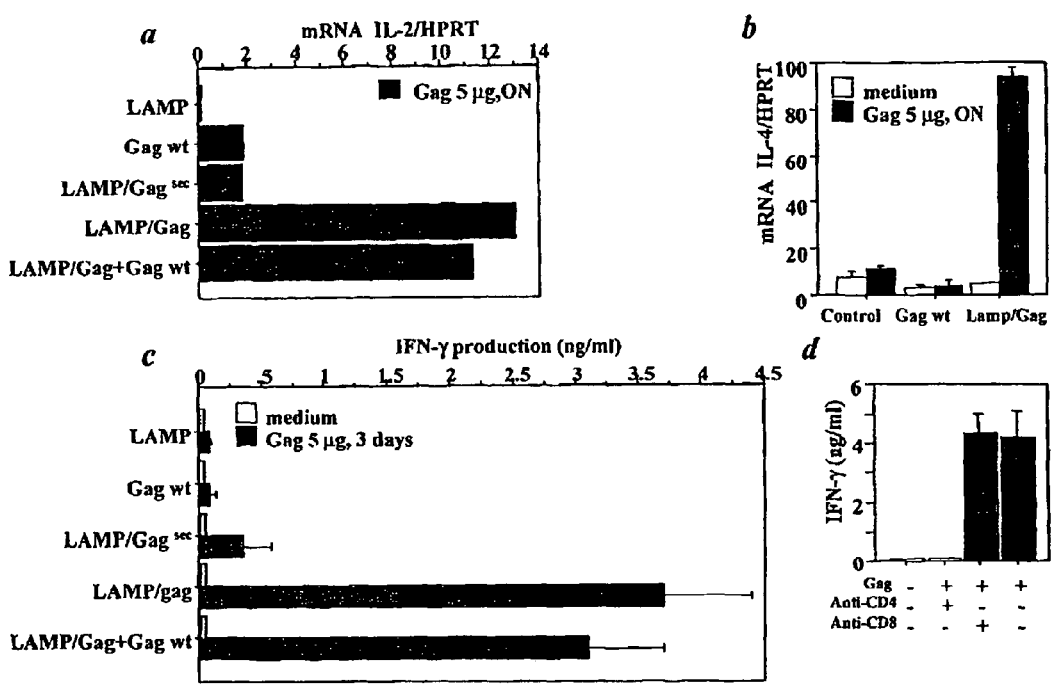

FIG. 7A-D LAMP/Gag chimera strongly enhances antigen-specific CD4-mediated cytokine responses. Data were obtained from splenocytes of mice immunized twice with the indicated plasmid DNA and incubated with p55Gag protein as indicated. Results are means ± S.D. a, Gag-specific up-regulation of IL-2 mRNA expression. b, Gag-specific up-regulation of IL-4 mRNA expression. c, Gag-specific induction of IFN-γ production. d, Gag-specific induction of IFN-γ production by splenocytes incubated with blocking antibodies and Gag as indicated.

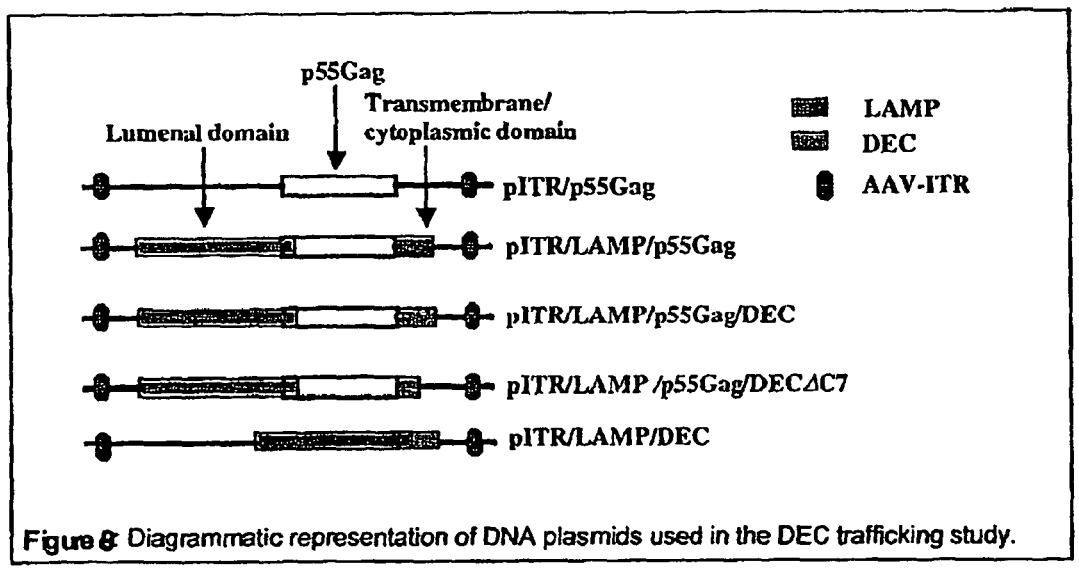
Figure 8: Diagrammatic representation of DNA plasmids used in the DEC trafficking study.

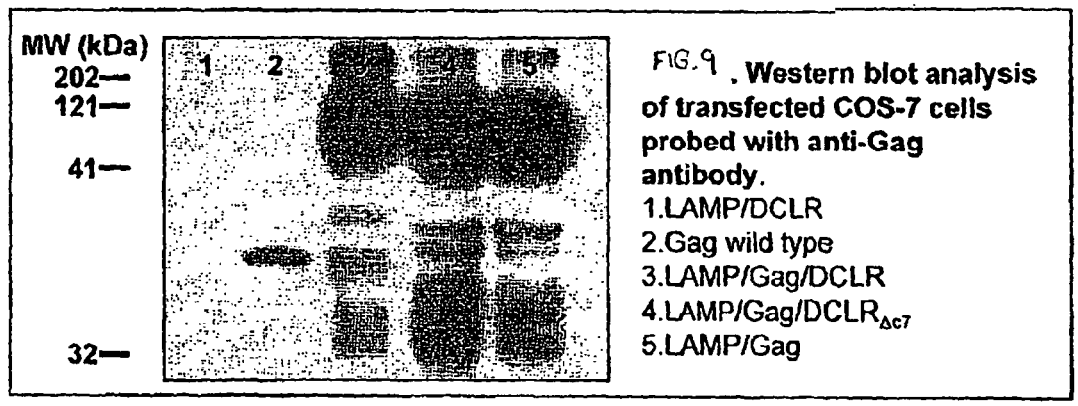

FIGURES 10A-F
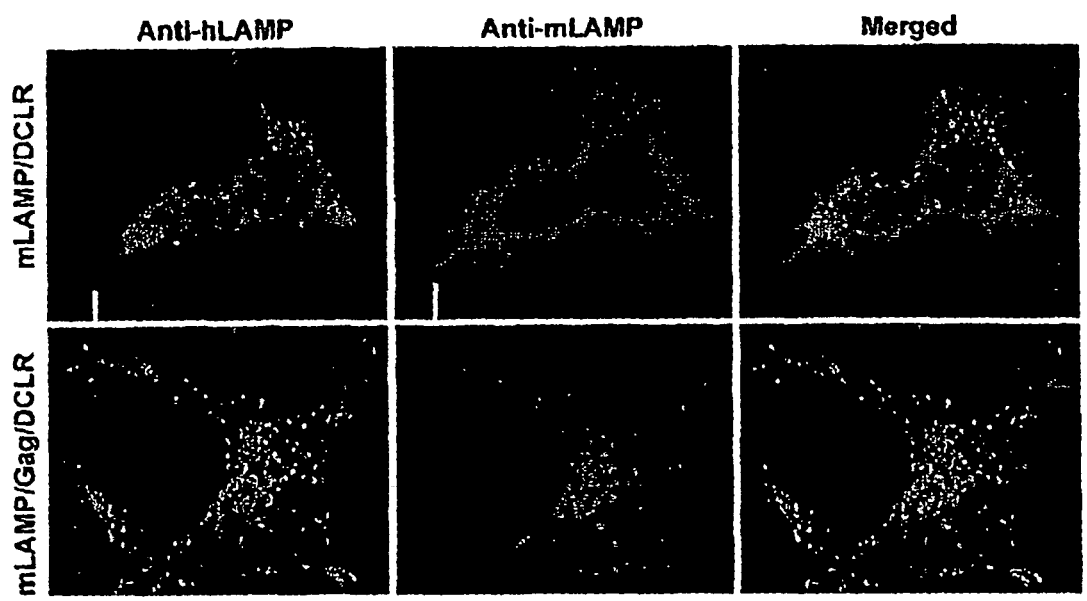
Immunoflourescence microscopy of human 293 cells transfected and stained as indicated. Upper row: transfected with mLAMP/DCLR. Lower row: transfected with mLAMP/Gag/DCLR. Left column: stained with anti-hLAMP; middle column: stained with anti-mLAMP-1; right column: overlapping images.

FIGURES 11A-C3
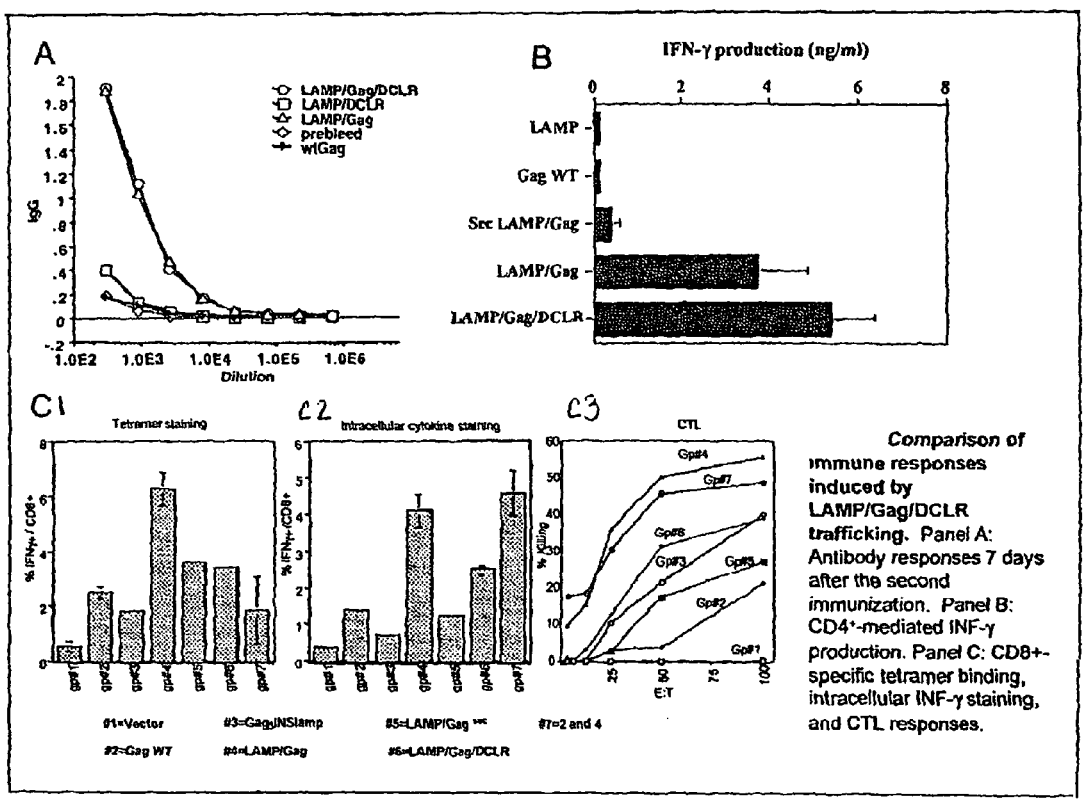

CHIMERIC VACCINES

RELATED APPLICATIONS

This application claims priority under 35 U.S.C. §119(e) to U.S. Provisional Application No. 60/281,607, U.S. Provisional Application 60/281,608, and U.S. Provisional Application 60/281,621, all filed Apr. 5, 2001. The entireties of these applications are incorporated by reference herein.

GOVERNMENT GRANTS

The work contained in this application was performed under government grant A1 41908 from the National Institutes of Health. The government may have certain rights in this invention.

FIELD OF THE INVENTION

The invention relates to chimeric vaccines comprising antigen sequences and trafficking domains, nucleic acids encoding the same, and methods for using the same.

BACKGROUND OF THE INVENTION

Antigen recognition and response in the mammalian immune system is governed, in part, by the interaction between T-cells and antigen presenting cells. Via its heterodimeric T cell receptor, a T cell recognizes peptide fragments of antigens presented as a complex with major histocompatibility (MHC) molecules (Yewdell and Bennenk, *Cell* 62: 203, 1990; Davis and Bjorkman, *Nature* 334: 395, 1988). There are two parallel cellular systems of T cells and antigen presenting molecules which distinguish between two types of antigens, foreign antigens introduced from outside of the cell (such as foreign chemicals, bacteria, and toxins) and endogenous antigens produced within the cell (such as viruses or oncogene products) (Bevan, *Nature* 325: 192, 1987; Braciale, et al., *Immunol. Rev.* 98:95, 1987; Germain, *Nature* 322: 687, 1986).

There are two general classes of MHC molecules, MHC class I, and MHC class II molecules. MHC class I molecules present peptide antigens generally derived from endogenously produced proteins to the $CD8^+ T_c$ cells, the predominant cytotoxic T cell that is antigen specific. The MHC class I-related proteolytic system is present in virtually all cells for the purpose of degrading highly abnormal proteins and short-lived molecules or viral proteins. This proteolysis is thought to be non-lysosomal and to involve ATP-dependent covalent conjugation to the polypeptide ubiquitin (Goldberg, et al., *Nature* 357: 375, 1992). Peptide fragments, possibly in association with a larger proteasome complex, are then postulated to enter into the endoplasmic reticulum or some other type of exocytic compartment (other than the endocytic/lysosomal compartment). There they bind to MHC class I molecules and follow the constitutive secretory pathway from the endoplasmic reticulum through the Golgi to the cell surface where they are presented by the MHC I protein to the CD3-CD8 cytotoxic T cell antigen receptor.

MHC class II molecules generally present antigens that are introduced from outside the cells in a process that involves cellular uptake of molecules comprising the antigens, and generation of antigenic peptide fragments in endosomal/lysosomal organelles. The MHC class II-related process by which foreign antigens are processed in antigen presenting cells (APC) cells is generally believed to occur in an endocytic pathway. Antigens taken into the cell by fluid-phase pinocytosis, absorptive endocytosis, or phagocytosis enter into a late endosomal/lysosomal compartment where large molecules are converted to peptides by digestion through proteases and other hydrolases. During this process, the immunodominant smaller peptides come in contact with and are bound by MHC class II molecules and the peptides are carried to the cell surface. On the cell surface of APC, these short peptides in conjunction with MHC class II molecules bind the CD3-CD4 complex on the surface of helper T cells, activating the replication and immune function of these cells. Following this interaction, helper T cells release lymphokines that stimulate the proliferation and differentiation of leukocytes and inhibit their emigration from the site of infection. In general, the activation of helper T cells by peptide-loaded APC is required for optimal B cell and T cell action, and thus is necessary for proper immune system function.

The exact site of antigen processing and association of processed peptides with MHC class II in the endosomal/lysosomal pathway is as yet unclear. Data have been presented suggesting that MHC class II molecules meet with endocytosed proteins in the early endosomal compartment (Guagliardi, et al., *Nature* 343: 133, 1990). Partially processed antigens and easily degradable antigens may yield peptides that can combine with MHC class II in the early endosomal compartment. However, evidence is mounting that the major site of antigen processing and association with MHC class II occurs either in the late endosome, the lysosome, or a distinct compartment related to the lysosome (Neefjes, et al., *Cell* 61: 171, 1990).

The functions of the two types of T cells are significantly different, as implied by their names. Cytotoxic T cells eradicate intracellular pathogens and tumors by direct lysis of cells and by secreting cytokines such as γ interferon. Helper T cells also can lyse cells, but their primary function is to secrete cytokines that promote the activities of B cells (antibody-producing cells) and other T cells and thus they broadly enhance the immune response to foreign antigens, including antibody-mediated and $T_c$-mediated response mechanisms.

$CD4^+$ T cells are the major helper T cell phenotype in the immune response. Their predominant function is to generate cytokines which regulate essentially all other functions of the immune response. Animals depleted of $CD4^+$ or humans depleted of $CD4^+$ cells (as in patients with AIDS) fail to generate antibody responses, cytotoxic T cell responses, or delayed type hypersensitivity responses. It is well known in the art that helper T cells are critical in regulating immune responses.

$CD4^+$ MHC class II restricted cells have also been shown to have cytotoxic capacity in a number of systems. One of the most important disease-relevant cases in which $CD4^+$ cytotoxic T cells have been demonstrated is in the response to fragments of the HIV gp120 protein (Polydefkis, et al., *J. Exp. Med.* 171: 875, 1990). $CD4^+$ MHC class II restricted cells also have been shown to be critical in generating systemic immune responses against tumors. In an adoptive transfer model, $CD4^+$ cells are critical in eliminating FBL tumors in mice. In the active immunotherapy model of Golumbek, et al. *Science* 254: 713, 1991, $CD4^+$ cells have also been shown to be critical in the systemic immune response against a number of different solid malignancies.

Because $CD4^+$MHC class II restricted cells appear to be the critical memory cells in the T cell arm of the immune response, an appropriate vaccination strategy is to generate $CD4^+$ antigen-specific MHC class II-restricted memory T cell populations.

Traditional vaccines rely on whole organisms, either pathogenic strains that have been killed or strains with attenuated pathogenicity. On the one hand, these vaccines run the risk of introducing the disease they are designed to prevent if the attenuation is insufficient or if enough organisms survive the killing step during vaccine preparation. On the other hand, such vaccines have reduced infectivity and are often insufficiently immunogenic, resulting in inadequate protection from the vaccination.

Recently, molecular biological techniques have been used in an attempt to develop new vaccines based on individual antigenic proteins from the pathogenic organisms. Conceptually, use of antigenic peptides rather than whole organisms would avoid pathogenicity while providing a vaccine containing the most immunogenic epitopes. However, it has been found that pure peptides or carbohydrates tend to be weak immunogens, seeming to require a chemical adjuvant in order to be properly processed and efficiently presented to the immune system. A vaccine dependent on T cell responses should contain as many T cell epitopes as would be needed to stimulate immunity in a target population of diverse MHC types. Further, since T cell recognition requires intracellular protein processing, vaccine preparations facilitating internalization and processing of antigen should generate a more effective immune response. Previous attempts to direct antigens to MHC molecules (see, U.S. Pat. No. 4,400,276) were not effective because the antigen-processing step was evaded. A successful hepatitis B vaccine has been prepared using cloned surface antigen of the hepatitis B virus, but this appears to be due to the tendency of the hepatitis surface antigen molecule to aggregate, forming regular particles that are highly immunogenic.

Genetic (DNA) vaccines are new and promising candidates for the development of both prophylactic and therapeutic vaccines. They are proven to be safe and the lack of immune responses to a vector backbone may be a definitive advantage if repetitive cycles of vaccination are required to achieve clinical benefits. However, one potential disadvantage of conventional DNA vaccines is their low immunogenicity in humans. One likely cause of this low immunogenicity is the restricted access of antigens formed within cells to the MHC II pathway for antigen processing and presentation to T helper cells.

U.S. Pat. No. 5,633,234 describe chimeric proteins comprising an antigenic domain and a cytoplasmic endosomal/lysosomal targeting signal which effectively target antigens to that compartment. The antigenic domain was processed and peptides from it presented on the cell surface in association with major histocompatibility (MHC) class II molecules. The cytoplasmic tail of LAMP-1 were used to form the endosomal/lysosomal targeting domain of the chimeric protein.

SUMMARY OF THE INVENTION

It is an object of this invention to provide vaccines with enhanced immunogenicity, particularly, genetic vaccines such as DNA or RNA vaccines.

It is a further object of this invention to provide more effective methods of vaccination, through the use of immunogens (regardless of whether they are derived from membrane or non-membrane proteins) which are directed to the lysosomal/endosomal compartment and related organelles (e.g., such as MIIC, CIIV, melanosomes, secretory granules, Birbeck granules, and the like) where they are processed and presented to major histocompatibility complex (MHC) class II molecules so that helper T cells are preferentially stimulated.

It is yet another object of this invention to provide improved methods of treatment for cancer by eliciting an anti-tumor immune response through stimulation of helper T cells.

In one aspect, the invention provides a chimeric protein, comprising: an N-terminal domain comprising at least one epitope of an antigen; and a trafficking domain; wherein the trafficking domain directs both membrane and non-membrane proteins to an endosomal compartment (e.g., a lysosome) in a cell. Preferably, the trafficking domain comprises the lumenal domain of a LAMP polypeptide, such as a LAMP-1 or LAMP-2 polypeptide.

In another aspect, the chimeric protein comprises a targeting sequence that directs the protein to an endosomal/lysosomal compartment or a related organelle for protein processing and peptide epitope binding to MHC II, such as the tetrapeptide sequence Tyr-Xaa-Xaa-Xbb, wherein Xaa is any amino acid and Xbb is a hydrophobic amino acid. In still another aspect, the targeting sequence comprises a dileucine sequence. In a further aspect, the targeting sequence comprises a cytosolic protein targeting domain from an endocytic receptor. Suitable domains, include, but are not limited to the targeting domain of a C-type lectin receptor, a DEC-205 polypeptide, gp200-MR6 protein, or homolog, ortholog, variant, or modified form thereof. MR6In one preferred aspect, the chimeric protein further comprises a Gag polypeptide. In one aspect, the Gag polypeptide is inserted into a portion of the lumenal domain of a LAMP polypeptide. More preferably, the protein further comprises a transmembrane domain and/or a signaling domain.

In one particularly preferred aspect, the protein comprises the lumenal domain of a LAMP polypeptide and a cytoplasmic domain comprising the tetrapeptide sequence Tyr-Xaa-Xaa-Xbb, wherein Xaa is any amino acid and Xbb is a hydrophobic aminio acid The chimeric protein, preferably, further comprises a transmembrane protein. Still more preferably, the chimeric protein also comprises a signaling domain.

Any type of antigen may be used to generate chimeric proteins. In one aspect, the antigen is selected from the group consisting of: a portion of an antigenic material from a pathogenic organism, a portion of an antigenic material from a cancer-specific polypeptide, and a portion of an antigenic material from a molecule associated with an abnormal physiological response (e.g., such as an autoimmune disease, an allergic reaction, cancer, or a congenital disease) or a response to a transplant or graft procedure. In another aspect, the antigenic material is from a pathogenic organism which is a virus, microorganism, or parasite. In a further aspect, the virus is an HIV virus. More than one antigen may be included in any chimeric protein.

The invention further provides a nucleic acid molecule encoding any of the chimeric proteins described above. The invention also provides a vector comprising the nucleic acid wherein the nucleic acid molecule is operably linked to an expression control sequence. In one preferred aspect, the vector is a vaccine vector, suitable for vaccinating a patient against the antigen. In another aspect, the invention provides a delivery vehicle comprising the nucleic acid molecule for facilitating the introduction of the nucleic acid molecule into a cell. The delivery vehicle may be lipid-based (e.g., a liposome formulation), viral-based (e.g., comprising viral proteins encapsulating the nucleic acid molecule), or cell-based In one preferred aspect, the vector is a vaccine vector.

The invention also provides a cell comprising any of the vectors described above. In one aspect, the cell is an antigen presenting cell. The antigen presenting cell may be a professional antigen presenting cell (e.g., a dendritic cell, macrophage, B cell, and the like) or an engineered antigen presenting cell (e.g., a non-professional antigen presenting cell engineered to express molecules required for antigen presentation, such as MHC class II molecules). The molecules required for antigen presentation may be derived from other cells, e.g., naturally occurring, or may themselves be engineered (e.g. mutated or modified to express desired properties, such as higher or lower affinity for an antigenic epitope). In one aspect, the antigen presenting cell does not express any co-stimulatory signals and the antigen is an auto-antigen.

The invention additionally provides a kit comprising a plurality of cells comprising any of the vectors described above. At least two of the cells express different MHC class II molecules, and each cell comprises the same vector. In one aspect, a kit is provided comprising a vector and a cell for receiving the vector.

The invention also provides a transgenic animal comprising at least one of the cells described above.

The invention further provides a method for generating an immune response in an animal to an antigen, comprising: administering to the animal a cell as described above, wherein the cell expresses, or can be induced to express, the chimeric protein in the animal. In one aspect, the cell comprises an MHC class II molecule compatible with MHC proteins of the animal, such that the animal does not generate an immune response against the MHC class II molecule. In one preferred aspect, the animal is a human.

In one aspect, the invention provides a method for eliciting an immune response to an antigen, comprising administering to an animal, any of the vectors described above. Preferably, the vector is infectious for a cell of the animal. For example, the vector may be a viral vector, such as a vaccinia vector. The antigen may be selected from the group consisting of: a portion of an antigenic material from a pathogenic organism, a portion of an antigenic material from a cancer-specific polypeptide, and a portion of an antigenic material from a molecule associated with an abnormal physiological response or a transplantation antigen. In one aspect, the pathogenic organism is a virus, microorganism, or parasite. In another aspect, the virus is an HIV virus. In still another aspect, the abnormal physiological response is an autoimmune disease, an allergic reaction, cancer, or a congenital disease.

In a further aspect, a cell is obtained from a patient, the vector is introduced into the cell and the cell or progeny of the cell is reintroduced into the patient. In one aspect, the cell is a stem cell-capable of differentiating into an antigen presenting cell. In another aspect, the cell does not express any co-stimulatory signals and the antigen is an autoantigen.

BRIEF DESCRIPTION OF THE FIGURES

The objects and features of the invention can be better understood with reference to the following detailed description and accompanying drawings.

FIG. 1A is a schematic representation of the different plasmid constructs. FIG. 1B is a Western blot analysis of COS cells transfected with different plasmids probed with anti-Gag). The horizontal arrows indicate the promoter region of the plasmids and the boxed areas represent the open reading frames. The separate boxes represent the different pieces of the protein chimeras indicated in the key below. TM/CYD boxes indicate the transmembrane and cytoplasmic domains included in the construct. The red diamonds indicate the AAV-ITRs added to the expression vector.

FIG. 2 shows an anti-HIV lysate antibody response in an average of individual mice (n=5). ELISA analysis of antibody binding to protein of an HIV-1 viral triton-X-100 lysate, 50 ul of 5 ug/ml added to plate.

FIG. 3 shows the titer of anti-HIV lysate antibody response in individual immunizations.

FIGS. 4A and B show an anti-HIV lysate antibody response at day 29 after the first immunization and 15 days after the second immunization; average of individual mice (n=6).

FIG. 5 shows an Interferon gamma and IL4 assay at day 45 after immunization with 50 µg DNA on days 0 and 30. Spleen cells were stimulated by medium (control), 5 µg Gag protein. LEFT: p55 Gag protein specific IL4 production. RIGHT: p55 Gag-specific INFγ production.

FIG. 6 shows a real-time IL-4 PCR assay at day 45 after immunization with 50 µg DNA on days 0 and 30. Spleen cells were stimulated by medium (control), and 5 µg Gag protein.

FIGS. 7A-D show effects of LAMP/Gag chimeras on antigen-specific CD4-mediated cytokine responses.

FIG. 8 shows vectors used to monitor trafficking of LAMP/Gag/DEC chimeras according to one aspect of the invention.

FIG. 9 shows Western Blot analysis of COS cells transfected with LAMP/Gag/DCLR chimeras.

FIGS. 10A-F show immunofluorescence of cells transfected with LAMP/Gag/DCLR chimeras.

FIGS. 11A-B, C1-C3 show comparisons of immune responses induced by LAMP/Gag/DCLR trafficking.

DETAILED DESCRIPTION

Figure 7E:
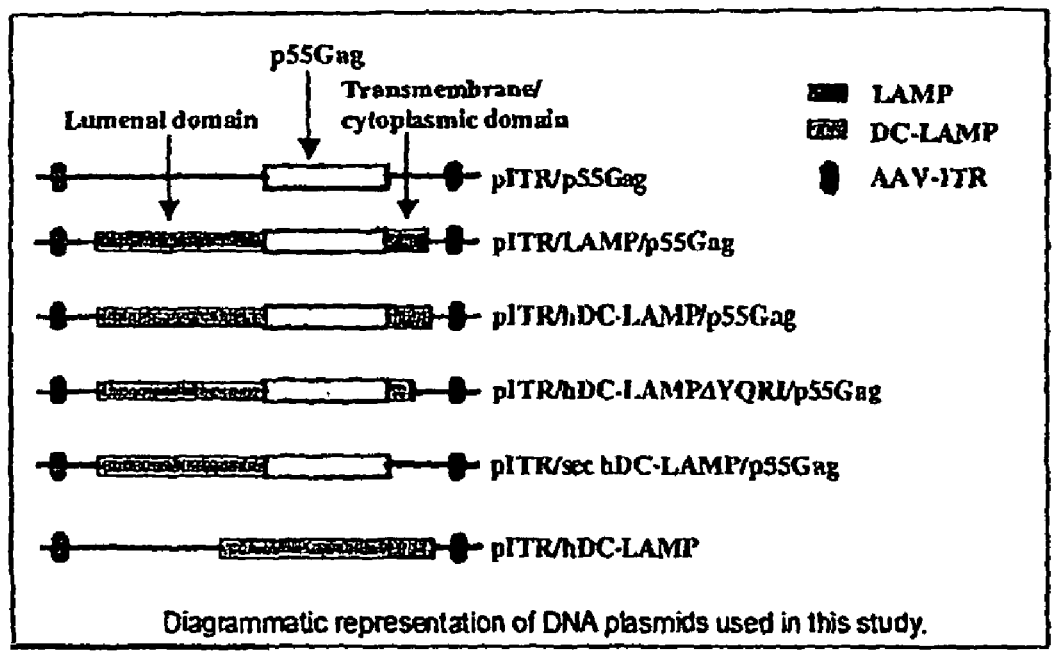
FIG. 7E shows various vectors encoding the chimeras.

The invention provides chimeric proteins and nucleic acids encoding these which can be used to generate vaccines against selected antigens. In one aspect, a chimeric protein comprises an antigen sequence and a domain for trafficking the protein to an endosomal/lysosomalcompartment or related organelle, irrespective of whether the antigen is derived from a membrane or non-membrane protein. In one preferred aspect, the trafficking domain comprises a lumenal domain of a LAMP polypeptide. Alternatively, or additionally, the chimeric protein comprises a trafficking domain of an endocytic receptor (e.g., such as C-type lectin, DEC-205 or gp200-MR6). The vaccines can be used to modulate or enhance an immune response. In one preferred aspect, the invention provides a method for treating a patient with cancer by providing a chimeric protein comprising a cancer-specific antigen or a nucleic acid encoding the protein to the patient.

DEFINITIONS

The following definitions are provided for specific terms which are used in the following written description.

As used in the specification and claims, the singular form "a", "an" and "the" include plural references unless the context clearly dictates otherwise. For example, the term "a cell" includes a plurality of cells, including mixtures thereof. The term "a nucleic acid molecule" includes a plurality of nucleic acid molecules.

As used herein, the term "comprising" is intended to mean that the compositions and methods include the recited elements, but do not exclude other elements. "Consisting essentially of", when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

As used herein, "the lysosomal/endosomal compartment" refers to membrane-bound acidic vacuoles containing LAMP molecules in the membrane, hydrolytic enzymes that function in antigen processing, and MHC class II molecules for antigen recognition and presentation. This compartment functions as a site for degradation of foreign materials internalized from the cell surface by any of a variety of mechanisms including endocytosis, phagocytosis and pinocytosis, and of intracellular material delivered to this compartment by specialized autolytic phenomena (de Duve, *Eur. J. Biochem.* 137: 391, 1983). The term "endosome" as used herein and in the claims encompasses a lysosome.

As used herein, a "lysosome-related organelle" refers to any organelle which comprises lysosymes and includes, but is not limited to, MIIC, CIIV, melanosomes, secretory granules, lytic granules, platelet-dense granules, basophil granules, Birbeck granules, phagolysosomes, secretory lysosomes, and the like. Preferably, such an organelle lacks mannose 6-phosphate receptors and comprises LAMP, but may or may not comprise an MHC class II molecule. For reviews, see, e.g., Blott and Griffiths, *Nature Reviews, Molecular Cell Biology*, 2002; Dell'Angelica, et al., *The FASEB Journal* 14: 1265-1278, 2000.

As used herein, the terms "polynucleotide" and "nucleic acid molecule" are used interchangeably to refer to polymeric forms of nucleotides of any length. The polynucleotides may contain deoxyribonucleotides, ribonucleotides, and/or their analogs. Nucleotides may have any three-dimensional structure, and may perform any function, known or unknown. The term "polynucleotide" includes, for example, single-, double-stranded and triple helical molecules, a gene or gene fragment, exons, introns, mRNA, tRNA, rRNA, ribozymes, antisense molecules, cDNA, recombinant polynucleotides, branched polynucleotides, aptamers, plasmids, vectors, isolated DNA of any sequence, isolated RNA of any sequence, nucleic acid probes, and primers. A nucleic acid molecule may also comprise modified nucleic acid molecules (e.g., comprising modified bases, sugars, and/or internucleotide linkers).

As used herein, the term "peptide" refers to a compound of two or more subunit amino acids, amino acid analogs, or peptidomimetics. The subunits may be linked by peptide bonds or by other bonds (e.g., as esters, ethers, and the like).

As used herein, the term "amino acid" refers to either natural and/or unnatural or synthetic amino acids, including glycine and both D or L optical isomers, and amino acid analogs and peptidomimetics. A peptide of three or more amino acids is commonly called an oligopeptide if the peptide chain is short. If the peptide chain is long (e.g., greater than about 10 amino acids), the peptide is commonly called a polypeptide or a protein. While the term "protein" encompasses the term "polypeptide", a "polypeptide" may be a less than full-length protein.

As used herein a "LAMP polypeptide" refers to LAMP-1, LAMP-2, CD63/LAMP-3, DC-LAMP, or any lysosomal associated membrane protein, or homologs, orthologs, variants (e.g., allelic variants) and modified forms (e.g., comprising one or more mutations, either naturally occurring or engineered). In one aspect, a LAMP polypeptide is a mammalian lysosomal associated membrane protein, e.g., such as a human or mouse lysosomal associated membrane protein. More generally, a "lysosomal membrane protein" refers to any protein comprising a domain found in the membrane of an endosomal/lysosomal compartment or lysosome-related organelle and which further comprises a lumenal domain.

As used herein, "an endocytic receptor" refers to a transmembrane protein with either its C-terminal or N-terminal facing the cytoplasm and which comprises a trafficking domain (e.g., a lumenal domain) for transporting a polypeptide or peptide conjugated to it (e.g., via an chemical bond) to an MHC class II molecule or to an intracellular compartment for subsequent association with an MHC class II molecule. Examples of endocytic receptors include, but are not limited to, Fc-receptors, complement receptors, scavenger receptors, integrins, lectins (e.g., C-type lectins), DEC-205 polypeptides, gp200-MR6 polypeptides, Toll-like receptors, heat shock protein receptors (e.g., CD 91), apoptotic body or necrotic body receptors (e.g., such as CD 14), or homologs, orthologs, variants (e.g., allelic variants) and modified forms thereof (e.g., comprising one or more mutations, either naturally occurring or engineered).

As used herein, "expression" refers to the process by which polynucleotides are transcribed into mRNA and/or translated into peptides, polypeptides, or proteins. If the polynucleotide is derived from genomic DNA, expression may include splicing of the mRNA transcribed from the genomic DNA.

As used herein, "under transcriptional control" or "operably linked" refers to expression (e.g., transcription or translation) of a polynucleotide sequence which is controlled by an appropriate juxtaposition of an expression control element and a coding sequence. In one aspect, a DNA sequence is "operatively linked" to an expression control sequence when the expression control sequence controls and regulates the transcription of that DNA sequence.

As used herein, "coding sequence" is a sequence which is transcribed and translated into a polypeptide when placed under the control of appropriate expression control sequences. The boundaries of a coding sequence are determined by a start codon at the 5' (amino) terminus and a translation stop codon at the 3' (carboxyl) terminus. A coding sequence can include, but is not limited to, a prokaryotic sequence, cDNA from eukaryotic mRNA, a genomic DNA sequence from eukaryotic (e.g., mammalian) DNA, and even synthetic DNA sequences. A polyadenylation signal and transcription termination sequence will usually be located 3' to the coding sequence.

As used herein, two coding sequences "correspond" to each other if the sequences or their complementary sequences encode the same amino acid sequences.

As used herein, "signal sequence" denotes the endoplasmic reticulum translocation sequence. This sequence encodes a signal peptide that communicates to a cell to direct a polypeptide to which it is linked (e.g., via a chemical bond) to an endoplasmic reticulum vesicular compartment, to enter an exocytic/endocytic organelle, to be delivered either to a cellular vesicular compartment, the cell surface or to secrete the polypeptide. This signal sequence is sometimes clipped off by the cell in the maturation of a protein. Signal sequences can be found associated with a variety of proteins native to prokaryotes and eukaryotes.

As used herein, "trafficking" denotes movement or progression of the polypeptide chimeric antigen through all of the cellular organelles or compartments in the pathway from the rough endoplasmic reticulum to the endosomal/lysosomal compartment or related organelles where antigen processing and binding to MHC II occurs. "Transport" refers to delivery of a chimeric protein to one particular type of cellular compartment.

As used herein, "targeting" denotes the polypeptide sequence that directs the trafficking of the polypeptide chimeric antigen to the preferred site or cellular organelles or compartment where antigen processing and binding to MHC II occurs.

As used herein, "a trafficking domain" refers to a series of continuous or discontinuous amino acids in a protein which are required for vesicular flow of the protein through one or more cellular compartments/organelles. A trafficking domain preferably comprises necessary sequences for proper protein folding to mediate this flow. In one aspect, a trafficking domain comprises a lumenal sequence; preferably, such a sequence comprises one or more binding sites for interactions with a cellular folding protein such as a chaperone.

In contrast, as used herein, a "targeting domain" refers to a series of amino acids which are required for deliver to a cellular compartment/organelle. Preferably, a targeting domain is a sequence which binds to an adaptor or AP protein (e.g., such as an AP1, AP2, or AP3 protein). Exemplary targeting domain sequences are described in Dell'Angelica, 2000, supra.

A "chimeric DNA" is an identifiable segment of DNA within a larger DNA molecule that is not found in association with the larger molecule in nature. Thus, when the chimeric DNA encodes a protein segment, the segment coding sequence will be flanked by DNA that does not flank the coding sequence in any naturally occurring genome. Allelic variations or naturally occurring mutational events do not give rise to a chimeric DNA as defined herein.

As used herein, a "nucleic acid delivery vector" is a nucleic acid molecule which can transport a polynucleotide of interest into a cell. Preferably, such a vector comprises a coding sequence operably linked to an expression control sequence. However, a polynucleotide sequence of interest may not necessarily comprise a coding sequence. For example, in one aspect a polynucleotide sequence of interest is an aptamer which binds to a target molecule. In another aspect, the sequence of interest is a complementary sequence of a regulatory sequence which binds to a regulatory sequence to inhibit regulation of the regulatory sequence. In still another aspect, the sequence of interest is itself a regulatory sequence (e.g. for titrating out regulatory factors in a cell).

As used herein, a "nucleic acid delivery vehicle" is defined as any molecule or group of molecules or macromolecules that can carry inserted polynucleotides into a host cell (e.g., such as genes or gene fragments, antisense molecules, ribozymes, aptamers, and the like) and which occurs in association with a nucleic acid vector as described above.

As used herein, "nucleic acid delivery," or "nucleic acid transfer," refers to the introduction of an exogenous polynucleotide (e.g., such as a "transgene") into a host cell, irrespective of the method used for the introduction. The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome.

As used herein, a "viral vector" refers to a virus or viral particle that comprises a polynucleotide to be delivered into a host cell, either in vivo, ex vivo or in vitro. Examples of viral vectors include, but are not limited to, adenovirus vectors, adeno-associated virus vectors, retroviral vectors, and the like. In aspects where gene transfer is mediated by an adenoviral vector, a vector construct refers to the polynucleotide comprising the adenovirus genome or part thereof, and a selected, non-adenoviral gene, in association with adenoviral capsid proteins.

As used herein, "adenoviral-mediated gene transfer" or "adenoviral transduction" refers to the process by which a gene or nucleic acid sequences are transferred into a host cell by virtue of the adenovirus entering the cell. Preferably, the virus is able to replicate and/or integrate and be transcribed within the cell.

As used herein, "adenovirus particles" are individual adenovirus virions comprised of an external capsid and internal nucleic acid material, where the capsid is further comprised of adenovirus envelope proteins. The adenovirus envelope proteins may be modified to comprise a fusion polypeptide which contains a polypeptide ligand covalently attached to the viral protein, e.g., for targeting the adenoviral particle to a particular cell and/or tissue type.

As used herein, the term "administering a molecule to a cell" (e.g., an expression vector, nucleic acid, an accessory factor, a delivery vehicle, agent, and the like) refers to transducing, transfecting, microinjecting, electroporating, or shooting the cell with the molecule. In some aspects, molecules are introduced into a target cell by contacting the target cell with a delivery cell (e.g., by cell fusion or by lysing the delivery cell when it is in proximity to the target cell).

As used herein, "hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

As used herein, a polynucleotide or polynucleotide region (or a polypeptide or polypeptide region) which has a certain percentage (for example, at least about 50%, at least about 60%, at least about 70%, at least about 80%, at least about 85%, at least about 90%, at least about 95%, at least about 99%) of "sequence identity" to another sequence means that, when maximally aligned, using software programs routine in the art, that percentage of bases (or amino acids) are the same in comparing the two sequences.

Two sequences are "substantially homologous" or "substantially similar" when at least about 50%, at least about 60%, at least about 70%, at least about 75%, and preferably at least about 80%, and most preferably at least about 90 or 95% of the nucleotides match over the defined length of the DNA sequences. Similarly, two polypeptide sequences are "substantially homologous" or "substantially similar" when at least about 50%, at least about 60%, at least about 66%, at least about 70%, at least about 75%, and preferably at least about 80%, and most preferably at least about 90 or 95% of the amino acid residues of the polypeptide match over a defined length of the polypeptide sequence. Sequences that are substantially homologous can be identified by comparing the sequences using standard software available in sequence data banks. Substantially homologous nucleic acid sequences also can be identified in a Southern hybridization experiment under, for example, stringent conditions as defined for that particular system. Defining appropriate hybridization conditions is within the skill of the art.

As used herein, a "trafficking sequence" which is substantially homologous to another trafficking sequence is one which shares substantial homology to the other trafficking sequence; however, the ultimate test for substantial homology is a functional assay in which a polypeptide comprising a substantially sequence substantially homologous to a trafficking sequence is able to co-localize to the same endosomal compartment as the trafficking sequence.

"Conservatively modified variants" of domain sequences also can be provided. With respect to particular nucleic acid sequences, conservatively modified variants refers to those nucleic acids which encode identical or essentially identical amino acid sequences, or where the nucleic acid does not encode an amino acid sequence, to essentially identical sequences. Specifically, degenerate codon substitutions can be achieved by generating sequences in which the third position of one or more selected (or all) codons is substituted with mixed-base and/or deoxyinosine residues (Batzer, et al., 1991, *Nucleic Acid Res.* 19: 5081; Ohtsuka, et al., 1985, *J. Biol. Chem.* 260: 2605-2608; Rossolini et al., 1994, *Mol. Cell. Probes* 8: 91-98).

The term "biologically active fragment", "biologically active form", "biologically active equivalent" of and "functional derivative" of a wild-type protein, possesses a biological activity that is at least substantially equal (e.g., not significantly different from) the biological activity of the wild type protein as measured using an assay suitable for detecting the activity. For example, a biologically active fragment comprising a trafficking domain is one which can colocalize to the same compartment as a full length polypeptide comprising the trafficking domain.

As used herein, "in vivo" nucleic acid delivery, nucleic acid transfer, nucleic acid therapy" and the like, refer to the introduction of a vector comprising an exogenous polynucleotide directly into the body of an organism, such as a human or non-human mammal, whereby the exogenous polynucleotide is introduced to a cell of such organism in vivo.

As used herein, the term "in situ" refers to a type of in vivo nucleic acid delivery in which the nucleic acid is brought into proximity with a target cell (e.g., the nucleic acid is not administered systemically). For example, in situ delivery methods include, but are not limited to, injecting a nucleic acid directly at a site (e.g., into a tissue, such as a tumor or heart muscle), contacting the nucleic acid with cell(s) or tissue through an open surgical field, or delivering the nucleic acid to a site using a medical access device such as a catheter.

As used herein, the term "isolated" means separated from constituents, cellular and otherwise, in which the polynucleotide, peptide, polypeptide, protein, antibody, or fragments thereof, are normally associated with in nature. For example, with respect to a polynucleotide, an isolated polynucleotide is one that is separated from the 5' and 3' sequences with which it is normally associated in the chromosome. As is apparent to those of skill in the art, a non-naturally occurring polynucleotide, peptide, polypeptide, protein, antibody, or fragments thereof, does not require "isolation" to distinguish it from its naturally occurring counterpart.

As used herein, a "target cell" or "recipient cell" refers to an individual cell or cell which is desired to be, or has been, a recipient of exogenous nucleic acid molecules, polynucleotides and/or proteins. The term is also intended to include progeny of a single cell, and the progeny may not necessarily be completely identical (in morphology or in genomic or total DNA complement) to the original parent cell due to natural, accidental, or deliberate mutation. A target cell may be in contact with other cells (e.g., as in a tissue) or may be found circulating within the body of an organism.

As used herein, a "subject" is a vertebrate, preferably a mammal, more preferably a human. Mammals include, but are not limited to, murines, simians, humans, farm animals, sport animals, and pets.

The terms "cancer," "neoplasm," and "tumor," are used interchangeably and in either the singular or plural form, refer to cells that have undergone a malignant transformation that makes them pathological to the host organism. Primary cancer cells transformation that makes them pathological to the host organism. Primary cancer cells (that is, cells obtained from near the site of malignant transformation) can be readily distinguished from non-cancerous cells by well-established techniques, particularly histological examination. The definition of a cancer cell, as used herein, includes not only a primary cancer cell, but any cell derived from a cancer cell ancestor. This includes metastasized cancer cells, and in vitro cultures and cell lines derived from cancer cells. When referring to a type of cancer that normally manifests as a solid tumor, a "clinically detectable" tumor is one that is detectable on the basis of tumor mass; e.g., by procedures such as CAT scan, MR imaging, X-ray, ultrasound or palpation, and/or which is detectable because of the expression of one or more cancer-specific antigens in a sample obtainable from a patient.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin *Remington's Pharm. Sci.,* 15th Ed. (Mack Publ. Co., Easton (1975)).

A cell has been "transformed", "transduced", or "transfected" by exogenous or heterologous nucleic acids when such nucleic acids have been introduced inside the cell. Transforming DNA may or may not be integrated (covalently linked) with chromosomal DNA making up the genome of the cell. In prokaryotes, yeast, and mammalian cells for example, the transforming DNA may be maintained on an episomal element, such as a plasmid. In a eukaryotic cell, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations (e.g., at least about 10).

As used herein, an "effective amount" is an amount sufficient to affect beneficial or desired results, e.g., such as an effective amount of nucleic acid transfer and/or expression, and/or the attainment of a desired therapeutic endpoint. An effective amount can be administered in one or more administrations, applications or dosages. In one aspect, an effective amount of a nucleic acid delivery vector is an amount sufficient to transform/transduce/transfect at least one cell in a population of cells comprising at least two cells.

As used herein, a "therapeutically effective amount" is used herein to mean an amount sufficient to prevent, correct and/or normalize an abnormal physiological response. In one aspect, a "therapeutically effective amount" is an amount sufficient to reduce by at least about 30 percent, more preferably by at least 50 percent, most preferably by at least 90 percent, a clinically significant feature of pathology, such as for example, size of a tumor mass, antibody production, cytokine production, fever or white cell count, etc.

An "antibody" is any immunoglobulin, including antibodies and fragments thereof, that binds a specific epitope. The term encompasses polyclonal, monoclonal, and chimeric antibodies (e.g., bispecific antibodies). An "antibody combining site" is that structural portion of an antibody molecule comprised of heavy and light chain variable and hypervariable regions that specifically binds antigen. Exemplary antibody molecules are intact immunoglobulin molecules, substantially intact immunoglobulin molecules, and those portions of an immunoglobulin molecule that contains the paratope, including Fab, Fab', F(ab')$_2$ and F(v) portions, which portions are preferred for use in the therapeutic methods described herein.

An "epitope" is a structure, usually made up of a short peptide sequence or oligosaccharide, that is specifically recognized or specifically bound by a component of the immune system. T-cell epitopes have generally been shown to be linear oligopeptides. Two epitopes correspond to each other if they can be specifically bound by the same antibody. Two epitopes correspond to each other if both are capable of binding to the same B cell receptor or to the same T cell receptor, and binding of one antibody to its epitope substantially prevents binding by the other epitope (e.g., less than about 30%, preferably, less than about 20%, and more preferably, less than about 10%, 5%, 1%, or about 0.1% of the other epitope binds).

The term "antigenic material" as used herein covers any substance that will elicit an innate or adaptive immune response.

The term "antigen presenting cell" as used herein intends any cell which presents on its surface an antigen in association with a major histocompatibility complex molecule, or portion thereof, or, alternatively, one or more non-classical MHC molecules, or a portion thereof. Examples of suitable APCs are discussed in detail below and include, but are not limited to, whole cells such as macrophages, dendritic cells, B cells, hybrid APCs, and foster antigen presenting cells.

As used herein an "engineered antigen-presenting cell" refers to an antigen-presenting cell that has a non-natural molecular moiety on its surface. For example, such a cell may not naturally have a costimulator on its surface or may have additional artificial costimulator in addition to natural costimulator on its surface, or may express a non-natural class II molecule on its surface.

As used herein, "immune effector cells" refers to cells capable of binding an antigen and which mediate an immune response. These cells include, but are not limited to, T cells, B cells, monocytes, macrophages, NK cells and cytotoxic T lymphocytes (CTLs), for example CTL lines, CTL clones, and CTLs from tumor, inflammatory, or other infiltrates.

An "isolated" or "purified" population of cells is substantially free of cells and materials with which it is associated in nature. By substantially free or substantially purified APCs is meant at least 50% of the population are APCs, preferably at least 70%, more preferably at least 80%, and even more preferably at least 90% free of non-APCs cells with which they are associated in nature.

As used herein, a "genetic modification" refers to any addition, deletion or disruption to a cell's normal nucleotides. Any method which can achieve the genetic modification of APCs are within the spirit and scope of this invention. Art recognized methods include viral mediated gene transfer, liposome mediated transfer, transformation, transfection and transduction, e.g., viral-mediated gene transfer such as the use of vectors based on DNA viruses such as adenovirus, adeno-associated virus and herpes virus, as well as retroviral based vectors.

The practice of the present invention employs, unless otherwise indicated, conventional molecular biology, microbiology, and recombinant DNA techniques within the skill of the art. Such techniques are explained fully in the literature. See, e.g., Maniatis, Fritsch & Sambrook, In *Molecular Cloning: A Laboratory Manual* (1982); *DNA Cloning: A Practical Approach*, Volumes I and II (D. N. Glover, ed., 1985); *Oligonucleotide Synthesis* (M. J. Gait, ed., 1984); Nucleic Acid Hybridization (B. D. Hames & S. J. Higgins, eds., 1985); *Transcription and Translation* (B. D. Hames & S. I. Higgins, eds., 1984); *Animal Cell Culture* (R. I. Freshney, ed., 1986); *Immobilized Cells and Enzymes* (IRL Press, 1986); B. Perbal, *A Practical Guide to Molecular Cloning* (1984).

Chimeric Vaccines

In U.S. Pat. No. 5,633,234, antigenic sequences were ligated to cytoplasmic domains of LAMP, transmembrane domains and signal sequences to form "antigen/LAMP chimeras". These chimeras were found to be directed to an endosomal/lysosomal trafficking pathway. With several membrane proteins, antigen/LAMP chimeras were found to elicit a much greater immune response than wild-type antigen.

This approach has proved useful in increasing cellular and humoral responses to several virus antigens, human papillomavirus E7, dengue virus membrane protein, HIV-1 gp160 membrane protein, HIV-1 p55 Gag, West Nile membrane protein, hepatitis C virus NS3 protein and cytomegalovirus pp65 (see, e.g., Bonini, et al., *J. Immunol.* 166: 5250-5257, 2001). The enhanced immune response can be attributed to co-localization of LAMP with MHC II and the more efficient processing and delivery of antigenic peptides. In addition, LAMP-targeting is reported to result in the presentation of an increased number of immunogenic epitopes, thus inducing a qualitatively broadened immune response compared to untargeted antigen. For example, Fernandes et al., 2000, *Eur. J. Immunol.* 30(8): 2333-43, demonstrated an increase in the number of presented peptides of a LAMP-trafficked OVA antigen encoded in a vaccinia vector. Of 12 peptides generated from exogenously supplied OVA, 9 were presented by an OVA/LAMP chimera, as compared to only 2 by the construct without LAMP.

However, while the cytoplasmic domain of LAMP is necessary (in conjunction with a signal sequence and transmembrane domain), it is not sufficient for endosomal/lysosomal trafficking. It is the discovery of the present invention that sequences of the lumenal domain of a lysosomal associated membrane protein such as a LAMP polypeptide are also required for the trafficking of some proteins to the lysosomal vesicular pathway.

For example, viral capsid or non-structural proteins, and other proteins not normally are not present in a membrane structure, do not track to a vesicular compartment occupied by LAMP and MHC II, and do not elicit an enhanced immune response. It is apparent that trafficking of proteins in a vesicular pathway requires more than a targeting signal, likely sequences that are involved in protein folding and interactions with other proteins that are involved in protein vesicular trafficking.

Therefore, the invention provides chimeras which comprise an antigen and lumenal sequences of a polypeptide that result in trafficking of the chimera to the endosomal/lysosomal compartment for antigen processing and antigen epitope association with MHC II. In one aspect, the chimeric protein additionally comprises cytoplasmic targeting sequences that direct the chimera to endosomal/lysosomal compartments. Additionally, the chimeric protein also may comprise a signal sequence and/or a transmembrane sequence. Suitable trafficking domains are provide by LAMP-1, LAMP-2, DC-LAMP, Trp-1, DEC-205, gp200-MR6, and other polypeptides, as discussed below. The signal sequence and transmembrane sequence may, but do not have to be, from these polypeptides. However, in one aspect, an antigen/LAMP chimera comprises a full length LAMP polypeptide.

Antigen Encoding Sequences

The present invention is widely applicable to antigenic materials that are of use in vaccines or in other contexts. This antigenic material will generally contain peptide segments that can be released by lysosomal enzymes and, when released, correspond to MHC class II epitopes. The antigenic material may also contain regions that stimulate other components of the immune system, including all immunoglobulin responses, and MHC I responses.

Because the constructs of the present invention traverse post-translational modification compartments prior to transport to the lysosomal compartment, the antigenic domain may also include epitopes resulting from cellular modification. Essentially, any polypeptide that can be synthesized by a mammalian cell and which contains B and T cell epitopes incorporated into antigenic domains, either directly in primary amino acid sequence or in signals directing its creation during post-translational processing may be used as a source of antigenic material.

Selection of the most appropriate portion of the desired antigen protein for use as the antigenic domain can be done by functional screening. Broadly, this screening method involves cloning DNA encoding one or more segments of the protein antigen; and at least a domain for trafficking the chimera to the endosomal/lysosomal compartment for antigen processing and antigen epitope association with MHC II. Preferably, such a construct will incorporate one or more DNA sequences encoding a signal sequence and/or transmembrane domain and/or a cytoplasmic targeting domain (e.g., such as the cytoplasmic tail of a LAMP polypeptide). The cloned DNA is expressed, preferably in an antigen presenting cell line (but not necessarily a professional antigen presenting cell).

The particular screening procedure depends upon the type of antigen and the assays for its antigenic activity. Antigenicity may be measured by stimulation of antigen-specific MHC class II specific T cell line or clone. Alternatively, antigenicity may be determined by measurement of the ability to generate antibodies or T cells specific for the antigen in vivo. These and other tests of antigenic activity are well known to those skilled in the art.

Antigens that may serve as the source of preferred antigenic material include tumor antigens, auto-antigens, transplantation antigens, cell surface proteins found on mammalian cells, cancer-specific proteins, proteins associated with abnormal physiological responses, proteins of bacteria, protozoa or fungi, including especially proteins found in the cell walls or cell membranes of these organisms, and proteins encoded by the genomes of viruses including retroviruses such as HIV and hepadnaviruses.

Particularly preferred antigens are antigens encoded by the genomes of organisms causative for, or associated with, hepatitis, rabies, malaria, parasitic infections (e.g., such as schistosomiasis), cancer, AIDS, yellow fever, dengue fever, Japanese encephalitis, West Nile fever, measles, smallpox, anthrax, Ebola, equine encephalitis, Rift valley fever, cat scratch fever, viral meningitis, plague, tularemia, and diseases caused by other pathogenic organisms. Particularly preferred viral antigens are virally-encoded proteins encoded by the genome of viruses pathogenic to man, horses, cows, pigs, llamas, giraffes, dogs, cats or chickens. Non-limiting examples include peptides from the influenza nucleoprotein composed of residues 365-80 (NP365-80), NP50-63, and NP147-58 and peptides from influenza hemagglutinin HA202-21 and HA523-45, defined previously in class I restricted cytotoxicity assays (Perkins et al., 1989, *J. Exp. Med.* 170: 279-289). Peptides representing epitopes displayed by the malarial parasite *Plasmodium falciparum* have been described (see, e.g., U.S. Pat. No. 5,609,872).

Antigenic materials also may include self-antigens recognized in transplant rejection, allergies, hypersensitivity responses, and autoimmune disorders. For example, the acetylcholine receptor (AChR) which is recognized in myasthenia gravis, may provide a source of antigenic materials. Another class of self-antigens for which antigenic epitopes have been described is human chorionic gonadotropin (hCG) beta subunit (see, e.g., U.S. Pat. No. 5,733,553). These epitopes find utility in contraceptive methods.

Synthetic antigens and altered antigens also can be used in the methods described herein. Synthetic antigenic peptide epitopes have modified amino acid sequences relative to their natural counterparts. Further encompassed by the term synthetic antigenic peptide" are multimers (concatemers) of a synthetic antigenic peptides, optionally including intervening amino acid sequences. For example, synthetic antigenic peptide epitopes of the present invention can be designed based on known amino acid sequences of antigenic peptide epitopes.

Other particularly preferred antigens include, but are not limited to, an HIV encoded polypeptide such as Gag, Env, Rev, Tat, and/or Nef polypeptides, gp160, and the like; papilloma virus core antigen; HCV structural and non-structural proteins; and CMV structural and non-structural proteins.

Also included within the scope of the invention are antigenic peptides that are differentially modified during or after translation, e.g., by phosphorylation, glycosylation, crosslinking, acylation, proteolytic cleavage, linkage to an antibody molecule, membrane molecule or other ligand, (Ferguson et al., *Ann. Rev. Biochem.* 57: 285-320, 1998).

New antigens and novel epitopes also can be identified using methods well known in the art. Any conventional method, e.g., subtractive library, comparative Northern and/or Western blot analysis of normal and tumor cells, Serial Analysis of Gene Expression (U.S. Pat. No. 5,695,937) and SPHERE (described in PCT WO 97/3 5 03 5), can be used to identify putative antigens for use.

For example, expression cloning as described in Kawakami et al., 1994, *Proc. Natl. Acad. Sci.* 91: 3515-19, also can be used to identify a novel tumor-associated antigen. Briefly, in this method, a library of cDNAs corresponding to mRNAs derived from tumor cells is cloned into an expression vector and introduced into target cells which are subsequently incubated with cytotoxic T cells. Pools of cDNAs that are able to stimulate T Cell responses are identified and through a process of sequential dilution and re-testing of less complex pools of cDNAs, unique cDNA sequences that are able to stimulate the T cells and thus encode a tumor antigen are identified. The tumor-specificity of the corresponding mRNAs can be confirmed by comparative Northern and/or Western blot analysis of normal and tumor cells.

SAGE analysis can be employed to identify the antigens recognized by expanded immune effector cells such as CTLs, by identifying nucleotide sequences expressed in the antigen-expressing cells. SAGE analysis begins with providing complementary deoxyribonucleic acid (cDNA) from an antigen-expressing population and cells not expressing the antigen. Both cDNAs can be linked to primer sites. Sequence tags are then created, for example, using appropriate primers to amplify the DNA. By measuring the differences in these tag sets between the two cell types, sequences which are aberrantly expressed in the antigen-expressing cell population can be identified.

Another method to identify optimal epitopes and new antigenic peptides is a technique known as Solid PHase Epitope REcovery ("SPHERE"). This method is described in detail in PCT WO 97/35035. Although used to screen for MHC class I-restricted CTL epitopes, the method can be modified to screen for class II epitopes by screening for the stimulation of antigen-specific MHC class II specific T cell lines, for example, rather than CTL. In SPHERE, peptide libraries are synthesized on beads where each bead contains a unique peptide that can be released in a controlled manner. Eluted peptides can be pooled to yield wells with any desired complexity. After cleaving a percentage of the peptides from the beads, these are assayed for their ability to stimulate a Class II response, as described above. Positive individual beads are then be decoded, identifying the reactive-amino acid sequence. Analysis of all positives will give a partial profile of conservatively substituted epitopes which stimulate the T cell response being tested. The peptide can be resynthesized and retested to verify the response. Also, a second library (of minimal complexity) can be synthesized with representations of all conservative substitutions in order to enumerate the complete spectrum of derivatives tolerated by a particular response. By screening multiple T cell lines simultaneously, the search for crossreacting epitopes can be facilitated.

Isolated peptides can be synthesized using an appropriate solid state synthetic procedure (Steward and Young, Solid Phase Peptide Synthesis, Freemantle, San Francisco, Calif. 1968). A preferred method is the Merrifield process (Merrifield, *Recent Progress in Hormone Res.* 23: 451, 1967). The antigenic activity of these peptides may conveniently be tested using, for example, the assays as described herein.

Once an isolated peptide is obtained, it may be purified by standard methods including chromatography (e.g., ion exchange, affinity, and sizing column chromatography), centrifugation, differential solubility, or by any other standard technique for protein purification. For immunoaffinity chromatography, an epitope may be isolated by binding it to an affinity column comprising antibodies that were raised against that peptide, or a related peptide, and were affixed to a stationary support. Alternatively, affinity tags such as hexa-His (Invitrogen), Maltose binding domain (New England Biolabs), influenza coat sequence (Kolodziej, et al., *Methods Enzymol.* 194: 508-509, 1991), and glutathione-S-transferase can be attached to the peptides to allow easy purification by passage over an appropriate affinity column. Isolated peptides also can be physically characterized using such techniques as proteolysis, nuclear magnetic resonance, and x-ray crystallography.

Having isolated and identified the peptide sequence of a desired epitope, nucleic acids comprising sequences encoding these epitopes can be sequenced readily.

Endocytic Trafficking Sequences

The available data suggest the following sequence of events in the intracellular transport of MHC class II molecules: MHC class II molecules with the invariant chain are assembled in the endoplasmic reticulum and transported through the Golgi in common with other membrane proteins including MHC class I. The molecules are then targeted to specific endosomal/lysosomal organelles by an unknown mechanism, segregating from the MHC class I molecules which follow a constitutive route to the cell surface. In the endocytotic/lysosomal route, the invariant chain is removed from MHC class II by proteases acting in an acidic environment. At the same time, antigenic fragments of proteins that have entered the endocytic/lysosomal pathway are generated by these proteases and the resulting peptides bind to the class II molecules and are carried to the cell surface.

The biosynthesis and vacuolar targeting mechanisms of the hydrolytic enzymes present in the lysosomal/endosomal compartment have been extensively studied (Kornfeld and Mellman, *Ann. Rev. Cell Biol.* 5: 483, 1989). Newly synthesized hydrolases in the Golgi apparatus acquire mannose 6-phosphate groups that serve as specific recognition markers for the binding of these enzymes to mannose 6-phosphate receptors which are then targeted in some unknown manner to a prelysosomal vacuole. There the receptor-enzyme complex is dissociated by low pH, and the receptors recycle to the Golgi apparatus, while the enzyme-containing vacuole matures into a lysosome.

The localization of the lysosomal membrane glycoproteins is controlled by a targeting mechanism independent of the well-defined mannose 6-phosphate receptor (MPR) pathway for hydrolytic lysosomal enzymes (Kornfeld and Mellman, 1989, supra). Recent studies describe a distinct vesicular compartment with lysosomal properties and characterized by high concentration of lysosomal-associated membrane protein (LAMP-1) and MHC class II molecules (Peters, et al., *EMBO J.* 9: 3497, 1990). Lysosomal/Endosomal Compartment Kinetic analysis of intracellular transport and targeting of newly synthesized LAMP-1 and other similar proteins indicate that the molecule is synthesized in the endoplasmic reticulum, processed in the Golgi cisternae and transported to lysosomes within one hour of its biosynthesis, without detectable accumulation in the plasma membrane (Barriocanal, et al., *J Biol. Chem.* 15: 261(35): 16755-63, 1986; D'Sousa, et al., *Arch. Biochem. Biophys.* 249: 522, 1986; Green, et al., *J. Cell Biol.,* 105: 1227, 1987).

Studies of the structure and function of the lysosomal membrane were initiated in 1981 by August and colleagues with the discovery of major cellular glycoproteins that were subsequently termed lysosomal-associated membrane proteins one and two (LAMP-1 and LAMP-2) due to their predominant localization in the lysosomal membrane (Hughes, et al., *J. Biol. Chem.* 256: 664, 1981; Chen, et al., *J. Cell Biol.* 101:85, 1985). Analogous proteins were subsequently identified in rat, chicken and human cells (Barriocanal, et al., 1986, supra; Lewis, et al., *J. Cell Biol.* 100:1839, 1985; Fambourgh, et al., *J. Cell Biol.* 106: 61, 1988; Mane, et al., *Arch. Biochem. Biophys.* 268: 360, 1989).

Typically, LAMP-1, as deduced from a cDNA clone (Chen, et al., *J. Biol. Chem.* 263: 8754, 1988) consists of a polypeptide core of about 382 amino acids with a large (346-residue) lumenal amino-terminal domain followed by a 24-residue hydrophobic transmembrane region and short (12-residue) carboxyl-terminal cytoplasmic tail. The lumenal domain is highly glycosylated, being substituted with about 20 asparagine linked complex-type oligosaccharides and consists of two to about 160-residue homology units that are separated by a proline/serine-rich region. Each of these homologous domains contains 4 uniformly spaced cysteine residues, disulfide bonded to form four 36-38-residue loops symmetrically placed within the two halves of the lumenal domain (Arterburn, et al., *J. Biol. Chem.* 265: 7419, 1990; see, also Chen, et al., *J. Biol. Chem.* 25: 263(18): 8754-8, 1988). The LAMP-2 molecule is highly similar to LAMP-1 in overall amino acid sequence (Cha, et al., *J. Biol. Chem.* 265: 5008, 1990).

LAMP-1 and LAMP-2 are not specifically found in antigen presenting cells (dendritic cells). Their precise function is unknown, but they presumably are involved in some manner with lysosome function. Their colocalization with MHC II in the multilaminar MIIC vesicular compartment of APCs has no known functional association to antigen processing or presentation; however, chimeric antigens comprising LAMP cytoplasmic domains, as discussed above, show enhanced immunogenicity (see, U.S. Pat. No. 5,633,234).

The invention provides chimeric proteins comprising the lumenal domain of a lysosomal associated membrane protein, such as a LAMP polypeptide, or a bioactive fragment or modified form thereof (collectively referred to as "a LAMP-lumenal domain"). In one aspect, the LAMP lumenal domain comprises at least two homology units. Preferably, each homology unit is separated by a proline/serine-rich region. More preferably, each homology domain comprises 4 cysteine residues capable of forming four 36-38-residue loops symmetrically placed within the two halves of the lumenal domain when disulfide bonded together. Most preferably, the lumenal domain comprises sequences necessary to target and traffic a polypeptide to which it is linked (e.g., via a chemical bond) to an endosomal/lysosomal compartment or lysosome-related organelle for binding to an MHC class II molecule or for delivery to another compartment/organelle where it will bind to an MHC class II molecule.

In another aspect, the chimeric protein additionally, or alternatively, comprises a dileucine-based signal comprising at least one leucine-leucine pair or at least one leucine/iso-leucine pair. Preferably, the protein further comprises an acidic residue 4-5 residues upstream of the pair. More preferably, this signal domain binds to an AP complex polypeptide (see, e.g., Bonafacino and Dell'Angelica, *J. Cell Biol.* 145: 923-926, 1999). Suitable dileucine-based domains can be found in tyrosinase (TM-$X_{10}$-EKQPLL-$X_5$-YHSL-$X_5$); TRP-2 (TM-$X_7$-EANQPLL-$X_{12}$); and Pmel7 (TM-$X_{34}$-ENSPLL-$X_5$) and P-protein (see, e.g., Dell'Angelica, 2000, supra), for example.

In a preferred aspect, the chimeric protein also comprises a cytoplasmic domain for targeting and/or trafficking a chimeric protein to an endosomal/lysosomal compartment or lysosome-related organelle. In one aspect, the cytoplasmic domain comprises the tail of a LAMP polypeptide. The eleven amino-acid sequence of the cytoplasmic tail of LAMP-1 and other similar lysosomal membrane glycoproteins has the following sequence: Arg-Lys-Arg-Ser-His-Ala-Gly-Tyr-Gln-Thr-Ile-COOH (Chen, et al., 1988, supra). In LAMP-1, these sequences are from amino acids 372-382 of the full-length polypeptide.

The known cytoplasmic tail sequences of lysosomal membrane proteins, LAMP-1 (Chen, et al., 1988, supra), LAMP-2 (Cha, et al., 1990, supra) and CD63 (Hotta, et al., *Cancer Res.* 48: 2955, 1988), have been aligned by the inventors with the Tyr-containing internalization signal in the cytoplasmic tail of LAP (Pohlman, et al., *EMBO J.* 7: 2343, 1988) in Table 1. The Tyr residue is known to be required for endosomal/lysosomal targeting, and it was demonstrated in U.S. Pat. No. 5,633,234 that the complete sequence required to target other molecules to lysosomes requires the Tyr-X-X-hyd sequence (i.e., a "Tyr motif"), a Tyr followed by two amino acids followed by a hydrophobic residue.

TABLE 1

Cytoplasmic Tail Sequences of the Major Lysosomal Membrane Proteins*

| LAMP-1: | RKRSHA GYQTI |
|---|---|
| LAMP-2: | KHHA GYEQF |
| CD63: | KSIRS GYEVM |
| LAP: | RMEAPP GYRHVADGQDHA |

*The conserved Gly-Tyr-X-X-hydrophobic residue motif in the cytoplasmic domain of the described lysosomal membrane proteins is underlined, where X is any amino acid. The complete cytoplasmic tail sequence of the listed proteins is shown from the transmembrane region to the carboxyl terminus.

The importance of a hydrophobic residue at or near the carboxyl-terminal position is shown by results obtained from modification of the Tyr-Gln-Thr-Ile sequence of LAMP-1. Mutant cDNA molecules in which Ile was substituted with two other hydrophobic residues, Leu or Phe, and a polar residue, Thr. Substituting Leu (Tyr-Gln-Thr-Leu) and Phe (Tyr-Gln-Thr-Phe) does not affect lysosomal targeting, whereas the Thr-containing mutant protein (Tyr-Gln-Thr-Thr) accumulates at the cell surface. Mutants containing Ala substituted for Gln (Tyr-Ala-Thr-Ile), Thr (Tyr-Gln-Ala-Ile), and both residues (Tyr-Ala-Ala-Ile) have no effect on targeting to the lysosomal membrane, indicating that these positions may be occupied by charged, polar, or nonpolar residues.

The preferred targeting signal to the lysosomal/endosomal compartment, therefore, includes a tetrapeptide sequence located in the cytoplasmic domain, near the transmembrane domain and also near the C-terminus. The cytoplasmic domain is preferably a short amino acid sequence (less than 70 amino acids, preferably less than 30 amino acids, most preferably less than 20 amino acids) ending in a free carboxyl group. In a more preferred embodiment, the tetrapeptide is at the C-terminal end of a short cytoplasmic tail that contains the targeting signal, or is in a context similar to LAMP-1.

A suitable four amino acid sequence for the tetrapeptide may be obtained by amino acid substitutions, so long as the motif consists of Tyr-X-X-Hyd (where X may be any amino acid and Hyd denotes a hydrophobic amino acid), and the ability to confer lysosomal/endosomal targeting is conserved. A particularly preferred tetrapeptide has the sequence Tyr-Gln-Thr-Ile. In the most preferred embodiment, the entire LAMP cytoplasmic tail in conjunction with its transmembrane domain, and most preferably, its luminal domain is coupled to the primary sequence of the antigenic domain for highly efficient MHC class II processing and presentation. However, the cytoplasmic domain is not necessary to facilitate trafficking so long as a lumenal domain of a LAMP polypeptide is provided.

In another aspect, the endosomal targeting domain comprises a transmembrane sequence. Many proteins that will serve as the source of the antigenic domain for particular immune stimulatory constructs will be surface antigens that include a transmembrane domain in their primary sequence. Such a transmembrane domain can be retained, and the cytoplasmic domain replaced with a lysosomal/endosomal targeting domain as taught herein (e.g., a domain comprising a LAMP lumenal domain).

In one preferred aspect, the transmembrane domain of LAMP (see, Chen, et al., *J. Biol. Chem.* 263: 8754, 1988) is coupled to the primary sequence of a desired antigenic domain and the sequence of the lumenal domain. The structure of a transmembrane domain in a polypeptide is well known in the art (see, e.g., Bangham, *Anal. Biochem.* 174: 142, 1988; Klein, et al., *Biochem. Biophys. Acta* 815: 468, 1985; Kyle & Doolittle, *J. Mol. Biol.* 157: 105, 1982). Usually the transmembrane region appears in the primary sequence as a sequence of 20-25 hydrophobic amino acid residues flanked by more hydrophilic regions. Such sequences can be found, for example, in most cell surface antigen sequences listed by Genebank as well as many other membrane proteins. The particular transmembrane sequence is not critical, so long as it serves to connect the antigenic domain to the lumenal domain and cytoplasmic tail and anchors the construct in the membranous compartment.

Additional, or alternative sorting motifs, can include, but are not limited to, one or more of: a targeting domain, a tyrosine motif domain as described above; a di-leucine and tyrosine-based domain; a proline rich domain; and S-V-V domain (see, e.g., Blott and Grifitts, *Nature* 3: 122-131, 2002). Endocytic Receptor Sequences Antigen access to the MHC II vesicular compartment of antigen presenting cells, such as dendritic cells, is normally by endocytosis of foreign antigens. It is the discovery of the instant invention that the trafficking domains of endocytic receptors can be used to generate chimeric polypeptides to carry antigens to endosomal/lysosomal compartments or to lysosome-related organelles for association with class II MHC molecules and subsequent processing.

In one aspect, therefore, the invention provides an antigen linked to a trafficking domain of an endocytic receptor (e.g., via in-frame fusion of nucleic acid sequences encoding the trafficking domain and antigen). The trafficking domain localizes the antigen to an endosomal/lysosomal compartment or to a lysosome-related organelle for association with an MHC class II molecule in the compartment/organelle or in a subsequent compartment to which the antigen is delivered.

Endocytic receptors according to the invention, include, but are not limited to receptors for microorganisms, Fc receptors (e.g., CD64, CD32, CD16, CD23, and CD89); complement receptors (e.g., CR1 or CD35, CR3, CR4); scavenger receptors or receptors which bind to acetylated or modified lipoproteins, polyribonucloetides, lipopolysaccharides and silica particles (e.g., such as SRA, MARCO), integrins (CD49e/CD29; CD49d/CD29; CD51/CD61); lectins (e.g., such as dectin-1, C-type lectins, and the like), and Toll-like receptors (e.g., TLRs). For a review of such receptors, see Underhill and Ozinsky, *Annu. Rev. Immunol.* 20: 825-52, 2002, for example.

In one aspect, the endocytic receptor is obtained from a professional antigen presenting cell such as a dendritic cell. A number of endocytic receptors of dendritic cells have been identified, including the macrophage mannose receptor (MMR), phospholipaseA$_2$-receptor, Endo 180, and DEC-205 and its human homologue, gp200-MR6 (McKay, et al., 1998). DEC-205 is reported to differ from the MMR, at least, in that it targets antigenic material to an endosomal/lysosomal compartment co-localized with LAMP and MHC II, whereas MMR is found in peripheral endosomes lacking LAMP and MHC II (Mahnke, et al., *J. Cell Biol.* 151(3): 673-684, 2000).

DEC-205 also demonstrates a greatly enhanced presentation of endocytosed antigen to CD4$^+$ T-cells, as compared to that by the MMR. This difference in trafficking and antigen delivery to MH II between the two molecules is reported to result from the presence in the cytosolic tail of DEC-205, in addition to the coated pit uptake sequence, of an EDE triad that is lacking in the MMR. The distal portion of the cytosolic tail containing the EDE sequence was shown to be required for the targeting to the deeper endosome/lysosome compartment containing LAMP and MHC II, and EDE was not replaced by an AAA sequence. Mahnke et al., 2000, supra, have also shown that these cytoplasmic tail trafficking signals are sufficient to traffic and recycle a CD 16 chimera to the MHC II/LAMP site and to mediate a 100-fold increase in antigen presentation.

The sequence similarity between DEC-205 and gp200-MR6, particularly, in the cytoplasmic domain, makes this sequence a suitable trafficking sequence as well. Further, gp200-MR6 has been shown to have the further important property of IL-4 regulation. McKay et al., *Eur J Immunol.* 28(12): 4071-83, 1998, have shown that ligation of gp200-MR6 can mimic IL-4 and have an antiproliferative, pro-maturational influence within the immune system, causing up-regulation of costimulatory molecules on B lymphocytes.

It is a discovery of the instant invention, however, that DEC-205 fusions with LAMP do not traffic to the endosomal compartment but rather localize to the cell surface. Chimeric proteins which combine LAMP domains, an antigen sequence containing at least one epitope, and endocytic receptor domains such as DEC-205 domains, however, are able to traffic to endosomal compartments, co-localizing with endogenous LAMP.

Therefore, in a preferred aspect, a chimeric protein of the invention comprises a lumenal domain of a lysosomal membrane polypeptide (e.g., such as a LAMP lumenal domain) and the targeting domain of an endocytic receptor (e.g., such as DEC-205 or gp 200-MR6 polypeptide). Such constructs not only show correct targeting but improved antigenicity as well. In a further aspect, both the targeting and trafficking domain of an endocytic receptor is provided along with the antigen domain comprising at least one epitope. Chimeric proteins may additionally, or alternatively, comprise the lumenal domain of an endocytic receptor. In still a further aspect, a chimeric protein may comprise a full-length endocytic receptor polypeptide along with the antigenic domain comprising at least one epitope.

In one aspect, the targeting domain of the endocytic receptor comprises the 31 amino acid cytoplasmic domain of a DEC polypeptide (see, e.g., Manhke, et al., 2000, supra). In another aspect, the targeting domain comprises residues 7-9 of the DEC-205 cytoplasmic tail. Preferably, the domain comprises a Tyr motif. More preferably, the targeting domain also comprises residues 18-27 of the DEC-205 cytoplasmic tail. In a further aspect, the targeting domain comprises an EDE domain. The sequence of DEC-205 is provided in Kato, et al., *Immunogenetics* 47(6): 442-50, 1998, while that of gp200-MR6 is provided in McKay, et al., 1998, supra, for example.

The chimeric protein may additionally comprise a cytoplasmic targeting domain for targeting a polypeptide to a endosomal/lysosomal compartment or a lysosome-related organelle (e.g., such as a cytoplasmic LAMP domain) as well as one or more of the other domains described above (e.g., signal sequence, transmembrane sequence, etc.). As above, additional, or alternative sorting motifs, can include, but are not limited to, one or more of the M6P domain; a tyrosine motif domain; a di-leucine and tyrosine-based domain; a proline rich domain; and S-V-V domain (see, e.g., Blott and Grifitts, Nature 3: 122-131, 2002).

Vaccine Compositions

Tumors re-express developmental or embryonic genes which are not expressed in normal cells in the individual. The major thrust of cancer immunotherapy is the identification of tumor specific antigens and the development of immunization strategies that will most effectively generate T cell dependent immunity against these antigens. For example, studies indicate that vaccinia virus recombinant vaccines containing either the SV40 T antigen genes or the E6 and E7 genes from HPV or influenza nucleoprotein will protect animals against subsequent challenges with tumor cells that express these proteins as tumor antigens. The protection is associated with the generation of antigen specific responses among T cells in host.

A number of genes encoding tumor-specific antigenic polypeptides have been identified. Such antigens include, but are not limited to a tumor antigen, e.g., a polypeptide comprising an epitope derived from gp 100, MAGE 1, MART, MUC I and tyrosinase-related-protein 1 and 2 (TRP-1, TRP-2) (see, e.g., Boon et al., *Immunol. Today* 16: 334-336, 1998). MARTI and gp 100 are melanocyte differentiation antigens specifically recognized by HLA-A2 restricted tumor-infiltrating lymphocytes (TILs) derived from patients with melanoma, and appear to be involved in tumor regression (Kawakami et al., *Proc. Natl. Acad. Sci. USA* 91:645 8-62, 1994; Kawakami, et al., *Proc. Natl. Acad. Sci. USA* 91: 3515-9).

EBV Epstein-Barr virus gene products also encode antigenic polypeptides which are expressed in Hodgkin's lymphomas as well as Burkits and other lymphomas. Products of the HTLV-1 genome have been found in adult T cell leukemia cells, while human papillomavirus (HPV) E6 and E7 gene products are found in cervical carcinoma cells.

Differential screening of nucleic acid sequences expressed by the two cell lines can be used to select sequences encoding antigens specific to cancer cells, and even specific stages of cancer cells. When the non-target cell is a normal cell, differential screening eliminates or reduces the nucleic acid sequences common to normal cells, thereby avoiding an immune response directed at antigens present on normal cells. When the non-target cell is a normal cell, differential screening eliminates or reduces sequences common to normal cells, thereby avoiding an immune response directed at antigens present on normal cells.

In many cases, it has been demonstrated that peptides derived from altered genetic sequences can associate with either MHC class I or MHC class II molecules and be recognized by the appropriate helper or cytotoxic T cells. Mutations in various oncogenes such as the position 12 mutation in K ras have been implicated as a major genetic alteration of colon cancer as well as other malignancies. Mutations in tumor suppressor genes, such as P53, are extremely common in many malignancies. Additionally, rearrangements that result in activation of oncogenes such as the rearrangement between the BCR and ab1 gene in chronic myelogenous leukemia generate novel protein sequences. Therefore, in one preferred aspect of the invention, the antigenic material used comprises a cancer-specific polypeptide or an altered polypeptide sequence (e.g., derived from a genetic mutation and/or chromosomal mutation) or which is more generally associated with an abnormal physiological response (e.g., an autoimmune response, a hypersensitivity reaction, a reaction to a transplant or graft, and the like).

Any strategy which would enhance the presentation of a particular antigen on MHC molecules of host antigen presenting cells would, in fact, enhance the immunization potential of such a viral based strategy for a disease such as cancer, or another abnormal physiological response. The equivalent arguments can be made for generation of enhanced vaccine efficacy for viral infections such as HIV.

Therefore, in one embodiment, this invention provides a vaccine composition for eliciting an immune response in a mammal to an antigen. The composition comprises a vaccine vector which comprises a chimeric DNA segment comprising a sequence encoding at least one epitope of an antigen. In one aspect, the sequence encoding the antigen is from the lumenal domain of a protein. Preferably, the DNA segment further includes a sequence encoding a lumenal domain of a lysosome associated membrane polypeptide (e.g., such as a LAMP polypeptide, homolog, ortholog, variant, or modified form thereof) or the trafficking domain of an endocytic receptor. Preferably, the lumenal domain or trafficking domain traffics the antigen to an endosomal/lysosomal compartment or to a lysosome-related organelle of a cell, where it binds to an MHC class II molecule or is processed for delivery to another compartment/organelle where it will subsequently bind to an MHC class II molecule. More preferably, the antigen is processed within the compartment/organelle (or subsequent compartment to which it is delivered) to generate an epitope which is presented on the surface of the cell and which is bound to the MHC class II molecule.

The vector also may encode one or more of a transmembrane domain, a cytoplasmic domain containing an endosomal/lysosomal targeting signal directing the protein to an endosomal/lysosomal compartment or lysosome-related organelle, a dileucine domain, a Tyr motif; a proline rich domain; and S-V-V domain.

The e domains may be provided in sequence or separated by nucleic acids encoding linker polypeptides or which encode other amino acid sequences with desired functionalities (e.g., protein stabilizing sequences, and the like). Generally, where linker sequences are included, these encode linker polypeptides which range from about one to about 50 amino acids. The minimal requirement of the vector is that it encode a chimeric protein with the desired trafficking properties. Such properties can be readily tested using assays routine in the art.

For example, immunofluorescence microscopy can be used to confirm the trafficking of a chimeric protein to an appropriate compartment/organelle. [$^{35}$S]methionine pulse-chase labeling analysis can be used to monitor the synthesis and degradation of the chimeric protein to demonstrate that the rates of synthesis of the chimeric protein vs. the endogenous protein comprising the antigen domain are essentially equal and/or that the processing of the chimeric protein occurs properly.

In particular embodiments, the protein encoded by the chimeric DNA segment contains an intralumenal domain comprising at least one epitope which is a peptide that complexes with major histocompatibility complex (MHC) class II molecules, an endosomal/lysosomal trafficking sequence as described above, and a cytoplasmic domain which contains an endosomal/lysosomal targeting sequence. Preferably, the targeting sequence comprises the tetrapeptide sequence Tyr-Xaa-Xaa-Xbb, wherein Xbb is a hydrophobic amino acid.

In another aspect, the protein encoded by the chimeric DNA segment comprises a full length lysosomal membrane associated polypeptide, such as a LAMP polypeptide, homolog, ortholog, variant or modified form thereof, which comprises sequences for targeting and trafficking both membrane-bound and non-membrane bound antigenic material to an endosomal/lysosomal compartment.

Recombinant Protein Chimera-Mediated Expression Of HIV-1 Gag Protein

In one aspect, the chimeric protein comprises an antigen from an HIV-encoded polypeptide. Induction of potent humoral and cellular immune responses, including those against viral structural genes have been shown to be crucial to HIV virus clearance. Specific-CD4 anti-Gag responses correlate with increased clinical resistance to the virus in HIV-infected patients and in a model of therapeutic vaccine in SIV-infected macaques. Therefore, in one preferred aspect, the antigen domain of the chimeric protein comprises a Gag epitope.

Gag is relatively conserved among diverse HIV strains and subtypes and broad cross-clad anti-Gag CTL responses have been demonstrated in HIV-infected patents. Studies of exposed but sero-negative subjects indicate that Gag-specific CTL may be involved in protection against the establishment of a persistant HIV infection. Additionally, Gag-specific $CD8^+$ cytotoxic T lymphocytes are important in controlling virus load during acute infection as well as during the asymptomatic stages of the infection. Multiple discrete Gag epitopes have been described and shown to mediate cytotoxic activities. Moreover, levels of p24-specific CTL proliferative responses of infected untreated persons were positively correlated with levels of Gag-specific CTL and negatively correlated with levels of plasma HIV-1 RNA.

The expression of the human immunodeficiency virus type 1 (HIV-1) gene when it is introduced into mammalian cells is tightly regulated at many levels. At a post-transcriptional step, the binding of HIV-1 Rev to an element of the Gag mRNA found in all unspliced and singly spliced HIV-1 mRNAs, the Rev-responsive element (RRE), results in the nuclear export of the mRNA and translation of Gag, Gag-Pol, Env, Vif, Vpr, and Vpu. In the absence of Rev, cells transfected with DNA encoding Gag produce little or no the Gag protein. Rev may also act to stabilize HIV-1 mRNAs by its effect on the high AU content instability sequences and its effect on certain cis-acting instability sequences (INS). (For a recent report, see Korsopoulou et al, 2000, for example).

The dependence on Rev for expression of the Gag protein is a severe problem for the use of this protein in the development of a Gag-based vaccine against HIV-1 with DNA plasmid vectors because of the requirement to provide an accessory factor for nuclear export of unspliced retroviral mRNA. Several procedures have been used by others to overcome the Rev dependence. The HIV-1 genes have an unusual codon bias, differing markedly from that of human genes, and humanizing the gene sequence has been found to enhance the translation of HIV-1 mRNAs (Haas, et al, *Curr Biol.* 6(3): 315-24, 1996). Similarly, removal of the INS sequences increases the translational efficiency (Schneider et al, *J. Virol.* 71(7): 4892-903, 1997). Others have also described certain cis active constitutive transport elements (CTE) present in the non-coding regions of simial type D retroviruses and lentiviruses (for a review see, Cullen, *Virology* 248: 203-210, 1998). This sequence folds into an extended RNA stem-loop structure which binds a transport associated protein (TAP) which promotes nucleocytoplasmic transport the mRNA.

In one aspect, the invention provides compositions to increase the protein expression of HIV-1 gag in the absence of HIV-1 Rev, a gene product normally required for its roles in HIV-1 mRNA translation and nuclear export. This expression of gag in cells transfected with a HIV-1 gag DNA plasmid is accomplished by synthesizing the gag gene as a DNA chimera encoding a gag sequence inserted into another highly expressed cellular protein. In one highly preferred aspect, the HIV-1 gag sequence is inserted into the lumenal domain of a lysosomal membrane protein, preferably, adjacent to a transmembrane domain. Such a chimera can be used to develop an anti-HIV-1 DNA vaccine comprising the gag gene.

DNA chimeric vaccines comprising nucleic acids encoding antigen sequences combined with nucleic acids encoding the targeting domains of an dendritic cell specific DEC-205 endocytic receptor and the lumenal trafficking domains of LAMP can be produced. In one aspect, the endocytic receptor is a dendritic cell endocytic receptor, such as DEC-205. As shown in the examples below, DEC-205 fused to a LAMP lumenal domain, HIV p55 gag, and the transmembrane and cytoplasmic tail of DEC-205 showed co-localizarion of the HIV antigen provided as part of the chimeric protein with the endogenous LAMP protein. The LAMP/Gag/DEC construct presented an equivalent immunogenicity to the LAMP/Gag construct.

Assembly of Sequences Encoding Chimeric Proteins

Procedures for construction of chimeric proteins are well known in the art (see e.g., Williams, et al., *J. Cell Biol.* 111: 955, 1990). DNA sequences encoding the desired segments can be obtained from readily available recombinant DNA materials such as those available from the American Type Culture Collection, 12301 Parklawn Drive, Rockville, Md. 20852, U.S.A., or from DNA libraries that contain the desired DNA.

Such DNA segments minimally include: sequences encoding an antigenic domain and a lumenal domain of a lysosomal membrane associated polypeptide for trafficking a polypeptide linked to the lumenal domain to an endosomal/lysosomal compartment or lysosome-related organelle and/or a trafficking domain of an endocytic receptor for trafficking to an endosomal/lysosomal compartment and or lysosome-related organelle. Additional DNA segments may include, but are not limited to, sequences encoding: cytoplasmic targeting sequences for targeting the chimeric protein to an endosomal/lysosomal compartment or lysosome-related organelle; transmembrane sequences, signal sequences, di-leucine sequences, Tyr motifs, proline rich domains, M6P sequences, Ser-Val-Val sequences and the like.

The DNA segments corresponding to the desired domain sequences are then assembled with appropriate control and signal sequences using routine procedures of recombinant DNA methodology. See, e.g., as described in U.S. Pat. No. 4,593,002, and Langford, et al., *Molec. Cell. Biol.* 6: 3191, 1986.

A DNA sequence encoding a protein or polypeptide can be synthesized chemically or isolated by one of several approaches. The DNA sequence to be synthesized can be designed with the appropriate codons for the desired amino acid sequence. In general, one will select preferred codons for the intended host in which the sequence will be used for expression. The complete sequence may be assembled from overlapping oligonucleotides prepared by standard methods and assembled into a complete coding sequence. See, e.g., Edge, *Nature* 292: 756, 1981; Nambair, et al. *Science* 223: 1299, 1984; Jay, et al., *J. Biol. Chem.* 259: 6311, 1984.

In one aspect, one or more of the nucleic acids encoding the domain sequences of the chimeric protein are isolated individually using the polymerase chain reaction (M. A. Innis, et al., In *PCR Protocols: A Guide To Methods and Applications*, Academic Press, 1990). The domains are preferably isolated from publicly available clones known to contain them, but they may also be isolated from genomic DNA or cDNA libraries. Preferably, isolated fragments are bordered by compatible restriction endonuclease sites which allow a chimeric DNA encoding the immunogenic protein sequence to be constructed. This technique is well known to those of skill in the art. Domain sequences may be fused directly to each other (e.g., with no intervening sequences), or inserted into one another (e.g., where domain sequences are discontinuous), or may separated by intervening sequences (e.g., such as linker sequences).

The basic strategies for preparing oligonucleotide primers, probes and DNA libraries, as well as their screening by nucleic acid hybridization, are well known to those of ordinary skill in the art. See, e.g., Sambrook, et al., 1989, supra;

Perbal, 1984, supra. The construction of an appropriate genomic DNA or cDNA library is within the skill of the art. See, e.g., Perbal, 1984, supra. Alternatively, suitable DNA libraries or publicly available clones are available from suppliers of biological research materials, such as Clonetech and Stratagene, as well as from public depositories such as the American Type Culture Collection.

Selection may be accomplished by expressing sequences from an expression library of DNA and detecting the expressed peptides immunologically. Clones which express peptides that bind to MHC II molecules and to the desired antibodies/T cell receptors are selected. These selection procedures are well known to those of ordinary skill in the art (see, e.g., Sambrook, et al., 1989, supra).

Once a clone containing the coding sequence for the desired polypeptide sequence has been prepared or isolated, the sequence can be cloned into any suitable vector, preferably comprising an origin of replication for maintaining the sequence in a host cell.

Nucleic Acid Delivery Vehicles

In one aspect, a nucleic acid vector encoding a chimeric vaccine is introduced into a cell. The cell may be a host cell for replicating the nucleic acid or for expressing the chimeric vaccine. Preferably, the host cell for expressing the chimeric vaccine is an antigen presenting cell (described further below).

The nucleic acid vector minimally comprises a polynucleotide sequence for insertion into a target cell and an expression control sequence operably linked thereto to control expression of the polynucleotide sequence (e.g., transcription and/or translation) in the cell. Examples include plasmids, phages, autonomously replicating sequences (ARS), centromeres, and other sequences which are able to replicate or be replicated in vitro or in a host cell (e.g., such as a bacterial, yeast, or insect cell) and/or target cell (e.g., such as a mammalian cell, preferably an antigen presenting cell) and/or to convey the sequences encoding the chimeric vaccine to a desired location within the target cell.

Recombinant expression vectors may be derived from micro-organisms which readily infect animals, including man, horses, cows, pigs, llamas, giraffes, dogs, cats or chickens. Preferred vectors include those which have already been used as live vaccines, such as vaccinia. These recombinants can be directly inoculated into a host, conferring immunity not only to the microbial vector, but also to express foreign antigens. Preferred vectors contemplated herein as live recombinant vaccines include RNA viruses, adenovirus, herpesviruses, poliovirus, and vaccinia and other pox viruses, as taught in Flexner, *Adv. Pharmacol.* 21: 51, 1990, for example.

Expression control sequences include, but are not limited to, promoter sequences to bind RNA polymerase, enhancer sequences or negative regulatory elements to bind to transcriptional activators and repressors, respectively, and/or translation initiation sequences for ribosome binding. For example, a bacterial expression vector can include a promoter such as the lac promoter and for transcription initiation, the Shine-Dalgarno sequence and the start codon AUG (Sambrook, et al., 1989, supra). Similarly, a eukaryotic expression vector preferably includes a heterologous, homologous, or chimeric promoter for RNA polymerase II, a downstream polyadenylation signal, the start codon AUG, and a termination codon for detachment of a ribosome.

Expression control sequences may be obtained from naturally occurring genes or may be designed. Designed expression control sequences include, but are not limited to, mutated and/or chimeric expression control sequences or synthetic or cloned consensus sequences. Vectors that contain both a promoter and a cloning site into which a polynucleotide can be operatively linked are well known in the art. Such vectors are capable of transcribing RNA in vitro or in vivo, and are commercially available from sources such as Stratagene (La Jolla, Calif.) and Promega Biotech (Madison, Wis.).

In order to optimize expression and/or transcription, it may be necessary to remove, add or alter 5' and/or 3' untranslated portions of the vectors to eliminate extra, or alternative translation initiation codons or other sequences that may interfere with, or reduce, expression, either at the level of transcription or translation. Alternatively, consensus ribosome binding sites can be inserted immediately 5' of the start codon to enhance expression. a wide variety of expression control sequences—sequences that control the expression of a DNA sequence operatively linked to it—may be used in these vectors to express the DNA sequences of this invention. Such useful expression control sequences include, for example, the early or late promoters of SV40, CMV, vaccinia, polyoma, adenovirus, herpes virus and other sequences known to control the expression of genes of mammalian cells, and various combinations thereof.

In one aspect, the nucleic acid delivery vector comprises an origin of replication for replicating the vector. Preferably, the origin functions in at least one type of host cell which can be used to generate sufficient numbers of copies of the sequence for use in delivery to a target cell. Suitable origins therefore include, but are not limited to, those which function in bacterial cells (e.g., such as *Escherichia* sp., *Salmonella* sp., *Proteus* sp., *Clostridium* sp., *Klebsiella* sp., *Bacillus* sp., *Streptomyces* sp., and *Pseudomonas* sp.), yeast (e.g., such as *Saccharamyces* sp. or *Pichia* sp.), insect cells, and mammalian cells. In one preferred aspect, an origin of replication is provided which functions in the target cell into which the nucleic acid delivery vehicle is introduced (e.g., a mammalian cell, such as a human cell). In another aspect, at least two origins of replication are provided, one that functions in a host cell and one that functions in a target cell.

The nucleic acid delivery vector may alternatively, or additionally, comprise sequences to facilitate integration of at least a portion of the nucleic acid deliver vector into a target cell chromosome. For example, the nucleic acid delivery vector may comprise regions of homology to target cell chromosomal DNA. In one aspect, the delivery vector comprises two or more recombination sites which flank a nucleic acid sequence encoding the chimeric vaccine.

The vector may additionally comprise a detectable and/or selectable marker to verify that the vector has been successfully introduced in a target cell and/or can be expressed by the target cell. These markers can encode an activity, such as, but not limited to, production of RNA, peptide, or protein, or can provide a binding site for RNA, peptides, proteins, inorganic and organic compounds or compositions and the like.

Examples of detectable/selectable markers genes include, but are not limited to: DNA segments that encode products which provide resistance against otherwise toxic compounds (e.g., antibiotics); DNA segments that encode products which are otherwise lacking in the recipient cell (e.g., tRNA genes, auxotrophic markers); DNA segments that encode products which suppress the activity of a gene product; DNA segments that encode products which can be readily identified (e.g., phenotypic markers such as β-galactosidase, a fluorescent protein (GFP, CFP, YFG, BFP, RFP, EGFP, EYFP, EBFP, dsRed, mutated, modified, or enhanced forms thereof, and the like), and cell surface proteins); DNA segments that bind products which are otherwise detrimental to cell survival and/or function; DNA segments that otherwise inhibit the activity of other nucleic acid segments (e.g., antisense oligonucleotides); DNA segments that bind products that modify a substrate (e.g., restriction endonucleases); DNA segments that can be used to isolate or identify a desired molecule (e.g., segments encoding specific protein binding sites); primer sequences; DNA segments, which when absent, directly or indirectly confer resistance or sensitivity to particular compounds; and/or DNA segments that encode products which are toxic in recipient cells.

The marker gene can be used as a marker for conformation of successful gene transfer and/or to isolate cells expressing transferred genes and/or to recover transferred genes from a cell. For example, in one aspect, the marker gene is used to isolate and purify antigen presenting cells expressing the chimeric vaccines.

As discussed above, homologs, variants, and modified forms of any of the domain sequences can be used so long as they retain the ability to function with their respective domain function. For example, a modified lumenal sequence must retain the ability to traffic both membrane and non-membrane antigenic materials to an endosomal compartment with at least about 50%, at least about 60%, at least about 80%, at least about 90%, or at least about 100% efficacy compared to the original domain sequence, i.e., an efficacy that results in sufficient antigen presentation by a cell comprising the chimeric sequence for it to mount an immune response. In one aspect, sequences containing a suitable trafficking signal may be identified by constructing a chimeric DNA containing the well-characterized antigenic domain of ovalbumin, a transmembrane domain, and the cytoplasmic domain of a protein containing a putative lysosomal/endosomal targeting signal. Efficiency of targeting can be measured by determining the ability of antigen presenting cells, expressing the chimeric protein, to stimulate HA epitope-specific, MHC class II restricted T-cells (see, e.g., Example 5 of U.S. Pat. No. 5,633, 234).

Substantially similar genes may be provided, e.g., genes with greater than about 50%, greater than about 70%, greater than about 90%, and preferably, greater than about 95% identity to a known gene. Percent identity can be determined using software programs known in the art, for example those described in *Current Protocols In Molecular Biology* (F. M. Ausubel et al., eds., 1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: http://www.ncbi.nlm.nih.gov/cgi-bin/BLAST.

"Conservatively modified variants" of genes also can be provided. With respect to particular nucleic acid sequences, conservatively modified variants refers to those nucleic acids which encode identical or essentially identical amino acid sequences, or where the nucleic acid does not encode an amino acid sequence, to essentially identical sequences. Specifically, degenerate codon substitutions can be achieved by generating sequences in which the third position of one or more selected (or all) codons is substituted with mixed-base and/or deoxyinosine residues (Batzer, et al., 1991, *Nucleic Acid Res.* 19: 5081; Ohtsuka, et al., 1985, *J. Biol. Chem.* 260: 2605-2608; Rossolini et al., 1994, *Mol. Cell. Probes* 8: 91-98).

Substantially similar domain sequences may initially be identified by selecting a sequence which specifically hybridizes to a domain sequence of interest under stringent hybridization conditions. Examples of stringent hybridization conditions include: incubation temperatures of about 25° C. to about 37° C.; hybridization buffer concentrations of about 6×SSC to about 10×SSC; formamide concentrations of about 0% to about 25%; and wash solutions of about 6×SSC. Examples of moderate hybridization conditions include: incubation temperatures of about 40° C. to about 50° C.; buffer concentrations of about 9×SSC to about 2×SSC; formamide concentrations of about 30% to about 50%; and wash solutions of about 5×SSC to about 2×SSC. Examples of high stringency conditions include: incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water. In general, hybridization incubation times are from 5 minutes to 24 hours, with 1, 2, or more washing steps, and wash incubation times are about 1, 2, or 15 minutes. SSC is 0.15 M NaCl and 15 mM citrate buffer. It is understood that equivalents of SSC using other buffer systems can be employed. Similarity can be verified by sequencing, but preferably, is also or alternatively, verified by function (e.g., ability to traffic to an endosomal compartment, and the like), using assays suitable for the particular domain in question.

Performing assays to determine the suitability of homologous, variant, or modified domain sequences is merely a matter of screening for sequences which express the appropriate activity. Such screening is routine in the art.

The nucleic acid delivery vector may be provided as naked nucleic acids or in a delivery vehicle associated with one or more molecules for facilitating entry of a nucleic acid into a cell. Suitable delivery vehicles include, but are not limited to: liposomal formulations, polypeptides; polysaccharides; lipopolysaccharides, viral formulations (e.g., including viruses, viral particles, artificial viral envelopes and the like), cell delivery vehicles, and the like.

Lipid-Based Formulations

Delivery vehicles designed to facilitate intracellular delivery of biologically active molecules must interact with both non-polar and polar environments (in or on, for example, the plasma membrane, tissue fluids, compartments within the cell, and the like). Therefore, preferably, delivery vehicles are designed to contain both polar and non-polar domains or a translocating sequence for translocating a nucleic acid into a cell.

Compounds having polar and non-polar domains are termed amphiphiles. Cationic amphiphiles have polar groups that are capable of being positively charged at, or around, physiological pH for interacting with negatively charged polynucleotides such as DNA.

The nucleic acid vectors described above can be provided in formulations comprising lipid monolayers or bilayers to facilitate transfer of the vectors across a cell membrane. Liposomes or any form of lipid membrane, such as planar lipid membranes or the cell membrane of an intact cell, e.g., a red blood cell, can be used. Liposomal formulations can be administered by any means, including administration intravenously or orally.

Liposomes and liposomal formulations can be prepared according to standard methods and are well known in the art, see, e.g., Remington's; Akimaru, 1995, *Cytokines Mol. Ther.* 1: 197-210; Alving, 1995, *Immunol. Rev.* 145: 5-31; Szoka 1980, *Ann. Rev. Biophys. Bioeng.* 9: 467; U.S. Pat. No. 4,235, 871; U.S. Pat. No. 4,501,728; and U.S. Pat. No. 4,837,028. In one aspect, the liposome comprises a targeting molecule for targeting a liposome:nucleic acid vector complex to a particular cell type. In a particularly preferred aspect, a targeting molecule comprises a binding partner (e.g., a ligand or receptor) for a biomolecule (e.g., a receptor or ligand) on the surface of a blood vessel or a cell found in a target tissue.

Liposome charge is an important determinant in liposome clearance from the blood, with negatively charged liposomes being taken up more rapidly by the reticuloendothelial system (Juliano, 1975, *Biochem. Biophys. Res. Commun.* 63: 651) and thus having shorter half-lives in the bloodstream. Incorporating phosphatidylethanolamine derivatives enhances the circulation time by preventing liposomal aggregation. For example, incorporation of N-(omega-carboxy)acylamidophosphatidylethanolamines into large unilamellar vesicles of L-alpha-distearoylphosphatidylcholine dramatically increases the in vivo liposomal circulation lifetime (see, e.g., Ahl, 1997, *Biochim. Biophys. Acta* 1329: 370-382). Liposomes with prolonged circulation half-lives are typically desirable for therapeutic and diagnostic uses. For a general discussion of pharmacokinetics, see, e.g., Remington's, Chapters 37-39, Lee, et al., In *Pharmacokinetic Analysis: A Practical Approach* (Technomic Publishing AG, Basel, Switzerland 1996).

Typically, liposomes are prepared with about 5 to 15 mole percent negatively charged phospholipids, such as phosphatidylglycerol, phosphatidylserine or phosphatidyl-inositol. Added negatively charged phospholipids, such as phosphatidylglycerol, also serve to prevent spontaneous liposome aggregation, and thus minimize the risk of undersized liposomal aggregate formation. Membrane-rigidifying agents, such as sphingomyelin or a saturated neutral phospholipid, at a concentration of at least about 50 mole percent, and 5 to 15 mole percent of monosialylganglioside can also impart desirably liposome properties, such as rigidity (see, e.g., U.S. Pat. No. 4,837,028).

Additionally, the liposome suspension can include lipid-protective agents which protect lipids against free-radical and lipid-peroxidative damages on storage. Lipophilic free-radical quenchers, such as alpha-tocopherol and water-soluble iron-specific chelators, such as ferrioxianine, are preferred.

The nucleic acid delivery vehicles of the invention can include multilamellar vesicles of heterogeneous sizes. For example, vesicle-forming lipids can be dissolved in a suitable organic solvent or solvent system and dried under vacuum or an inert gas to form a thin lipid film. If desired, the film can be redissolved in a suitable solvent, such as tertiary butanol, and then lyophilized to form a more homogeneous lipid mixture which is in a more easily hydrated powderlike form. This film is covered with an aqueous solution of the peptide or polypeptide complex and allowed to hydrate, typically over a 15 to 60 minute period with agitation. The size distribution of the resulting multilamellar vesicles can be shifted toward smaller sizes by hydrating the lipids under more vigorous agitation conditions or by adding solubilizing detergents such as deoxycholate. The hydration medium preferably comprises the nucleic acid at a concentration which is desired in the interior volume of the liposomes in the final liposome suspension.

Following liposome preparation, the liposomes can be sized to achieve a desired size range and relatively narrow distribution of liposome sizes. One preferred size range is about 0.2 to 0.4 microns, which allows the liposome suspension to be sterilized by filtration through a conventional filter, typically a 0.22 micron filter. Filter sterilization can be carried out on a high throughput basis if the liposomes have been sized down to about 0.2 to 0.4 microns. Several techniques are available for sizing liposome to a desired size (see, e.g., U.S. Pat. No. 4,737,323).

Suitable lipids include, but are not limited to, DOTMA (Felgner, et al., 1987, *Proc. Natl. Acad. Sci. USA* 84: 7413-7417), DOGS or Transfectain™ (Behr, et al., 1989, *Proc. Natl. Acad. Sci. USA* 86: 6982-6986), DNERIE or DORIE (Felgner, et al., *Methods* 5: 67-75), DC-CHOL (Gao and Huang, 1991, *BBRC* 179: 280-285), DOTAPTM (McLachlan, et al., 1995, *Gene Therapy* 2: 674-622), Lipofectamine® and glycerolipid compounds (see, e.g., EP901463 and WO98/37916).

Other molecules suitable for complexing with nucleic acid delivery vectors include cationic molecules, such as, polyamidoamine (Haensler and Szoka, 1993, *Bioconjugate Chem.* 4: 372-379), dendritic polysine (WO 95/24221), polyethylene irinine or polypropylene h-nine (WO 96/02655), polylysine (U.S. Pat. No. 5,595,897; FR 2 719 316), chitosan (U.S. Pat. No. 5,744,166), DNA-gelatin coarcervates (see, e.g., U.S. Pat. No. 6,207,195; U.S. Pat. No. 6,025,337; U.S. Pat. No. 5,972,707) or DEAE dextran (Lopata, et al., 1984, *Nucleic Acid Res.* 12: 5707-5717).

Viral-Based Gene Delivery Vehicles

In one aspect, the nucleic acid delivery vehicle comprises a virus or viral particle. In this aspect, preferably, the nucleic acid vector comprises a viral vector. Viral vectors, such as retroviruses, adenoviruses, adeno-associated viruses and herpes viruses, are often made up of two components, a modified viral genome and a coat structure surrounding it (see, e.g., Smith et al., 1995, *Ann. Rev. Microbiol.* 49: 807-838), although sometimes viral vectors are introduced in naked form or coated with proteins other than viral proteins. Most current vectors have coat structures similar to a wild-type virus. This structure packages and protects the viral nucleic acid and provides the means to bind and enter target cells.

Preferably, viral vectors are modified from wild-type viral genomes to disable the growth of the virus in a target cell while enabling the virus to grow in a host cell (e.g., such as a packaging or helper cell) used to prepare infectious particles. Vector nucleic acids generally essential cis-acting viral sequences for replication and packaging in a helper line and expression control sequences for regulating the expression of a polynucleotide being delivered to a target cell. Other viral functions are expressed in trans in specific packaging or helper cell lines as are known in the art.

Preferred vectors are viral vectors derived from a virus selected from the group consisting of herpes viruses, cytomegaloviruses, foamy viruses, lentiviruses, Semliki forrest virus, AAV (adeno-associated virus), poxviruses, adenovirases and retroviruses. Such viral vectors are well known in the art.

In one preferred aspect, a viral vector used is an adenoviral vector. The adenoviral genome consists of a linear double-stranded DNA molecule of approximately 36 kb carrying more than about thirty genes necessary to complete the viral replication cycle. The early genes are divided into 4 regions (E1 to E4) that are essential for viral replication with the exception of the E3 region, which is believed to modulate the anti-viral host immune response. The E1 region (EIA and EIB) encodes proteins responsible for the regulation of transcription of the viral genome. Expression of the E2 region genes (E2A and E2B) leads to the synthesis of the polypeptides needed for viral replication. The proteins encoded by the E3 region prevent cytolysis by cytotoxic T cells and tumor necrosis factor (Wold and Gooding, 1991, *Virology* 184: 1-8). The proteins encoded by the E4 region are involved in DNA replication, late gene expression and splicing and host cell shut off (Halbert, et al., 1985, *J. Virol.* 56: 250-257). The late genes generally encode structural proteins contributing to the viral capsid. In addition, the adenoviral genome carries at cis-acting 5' and 3' ITRs (Inverted Terminal Repeat) and packaging sequences essential for DNA replication. The ITRs harbor origins of DNA replication while the encapsidation region is required for the packaging of adenoviral DNA into infectious particles.

Adenoviral vectors can be engineered to be conditionally replicative (CRAd vectors) in order to replicate selectively in specific cells (e.g., such as proliferative cells) as described in Heise and Kim (2000, *J. Clin. Invest.* 105: 847-85 1). In another aspect, an adenoviral vector is replication-defective for the E1 function (e.g., by total or partial deletion or mutagenesis of E1). The adenoviral backbone of the vector may comprise additional modifications (deletions, insertions or mutations in one or more viral genes). An example of an E2 modification is illustrated by the thermosensitive mutation localized on the DBP (DNA Binding Protein) encoding gene (Ensinger et al., 1972, *J. Virol.* 10: 328-339). The adenoviral sequence may also be deleted of all or part of the E4 region (see, e.g., EP 974 668; Christ, et al., 2000, *Human Gene Ther.* 11: 415-427; Lusky, et al., 1999, *J. Virol.* 73: 8308-8319). Additional deletions within the non-essential E3 region may allow the size of the polynucleotide being delivered to be increased (Yeh, et al., 1997, *FASEB Journal* 11: 615 623). However, it may be advantageous to retain all or part of the E3 sequences coding for polypeptides (e.g., such as gp19k) allowing the virus to escape the immune system (Gooding, et al., 1990, *Critical Review of Immunology* 10: 53-71) or inflammatory reactions (EP 00440267.3).

Second generation vectors retaining the ITRs and packaging sequences and comprising substantial genetic modifications to abolish the residual synthesis of the viral antigens also may be used in order to improve long-term expression of the expressed gene in the transduced cells (see, e.g., WO 94/28152; Lusky, et al., 1998, *J. Virol* 72: 2022-2032).

The polynucleotide being introduced into the cell may be inserted in any location of the viral genome, with the exception of the cis-acting sequences. Preferably, it is inserted in replacement of a deleted region (E1, E3 and/or E4), preferably, within a deleted E1 region.

Adenoviruses can be derived from any human or animal source, in particular canine (e.g. CAV-1 or CAV-2 Genbank ref. CAVIGENOM and CAV77082, respectively), avian (Genbank ref. AAVEDSDNA), bovine (such as BAV3; Reddy, et al., 1998, *J. Virol.* 72: 1394 1402), murine (Genbank ref. ADRMUSMAVI), ovine, feline, porcine or simian sources or alternatively, may be a hybrid virus. Any serotype can be employed. However, the human adenoviruses of the C sub-group are preferred, especially adenoviruses 2 (Ad2) and 5 (Ad5). Such viruses are available, for example, from the ATCC.

Adenoviral particles or empty adenoviral capsids also can be used to transfer nucleic acid delivery vectors by a virus-mediated cointernalization process as described in U.S. Pat. No. 5,928,944. This process can be accomplished in the presence of cationic agent(s) such as polycarbenes or lipid vesicles comprising one or more lipid layers.

Adenoviral particles may be prepared and propagated according to any conventional technique in the field of the art (e.g., WO 96/17070) using a complementation cell line or a helper virus, which supplies in trans the missing viral genes necessary for viral replication. The cell lines 293 (Graham et al., 1977, *J. Gen. Virol.* 36: 59-72) and PERC6 (Fallaux et al., 1998, *Human Gene Therapy* 9: 1909-1917) are commonly used to complement E1 deletions. Other cell lines have been engineered to complement defective vectors (Yeh, et al., 1996, *J. Virol.* 70: 559-565; Kroughak and Graham, 1995, *Human Gene Ther.* 6: 1575-1586; Wang, et al., 1995, *Gene Ther.* 2: 775-783; Lusky, et al., 1998, *J. Virol.* 72: 2022-203; EP 919627 and WO 97/04119). The adenoviral particles can be recovered from the culture supernatant but also from the cells after lysis and optionally further purified according to standard techniques (e.g., chromatography, ultracentrifugation, as described in WO 96/27677, WO 98/00524 WO 98/26048 and WO 00/50573).

Cell-type specific targeting may be achieved with vectors derived from adenoviruses having a broad host range by the modification of viral surface proteins. For example, the specificity of infection of adenoviruses is determined by the attachment to cellular receptors present at the surface of permissive cells. In this regard, the fiber and penton present at the surface of the adenoviral capsid play a critical role in cellular attachment (Defer, et al., 1990, *J. Virol.* 64: 3661-3673). Thus, cell targeting of adenoviruses can be carried out by genetic modification of the viral gene encoding fiber and/or penton, to generate modified fiber and/or penton capable of specific interaction with unique cell surface receptors. Examples of such modifications are described in Wickarn, et al., 1997, *J. Virol.* 71: 8221-8229; Arriberg, et al., 1997, *Virol. Chem* 268: 6866-6869; Roux, et al., 1989, *Proc. Natl. Acad. Sci. USA* 86: 9079-9083; Miller and Vile, 1995, *FASEB J.* 9: 190-199; WO 93/09221, and in WO 95/28494.

In a particularly preferred aspect, adeno-associated viral sequences are used as vectors. Vectors derived from the human parvovirus AAV-2 (adeno-associated virus type 2) are among the most promising gene delivery vehicles currently being developed. Several of the features of this system for packaging a single-stranded DNA suggest it as a possible alternative to naked DNA for delivery of genetic vaccines. A primary attractive feature, in contrast to other viral vectors such as vaccinia or adenovirus, is that AAV vectors do not express any viral genes. The only viral DNA sequences included in the vaccine construct are the 145 bp inverted terminal repeats (ITR). Thus, as in immunization with naked DNA, the only gene expressed is that of the antigen, or antigen chimera. Additionally, AAV vectors are known to transduce both dividing and non-dividing cells, such as human peripheral blood monocyte-derived dendritic cells, with persistent transgene expression, and with the possibility of oral and intranasal delivery for generation of mucosal immunity. Moreover, the amount of DNA required appears to be much less by several orders of magnitude, with maximum responses at doses of $10^{10}$ to $10^{11}$ particles or copies of DNA in contrast to naked DNA doses of 50 µg or $\sim 10^{15}$ copies.

In one aspect, AAV vectors are packaged by co-transfection of a suitable cell line (e.g., human 293 cells) with the DNA contained in the AAV ITR chimeric protein encoding constructs and an AAV helper plasmid ACG2 containing the AAV coding region (AAV rep and cap genes) without the ITRs. The cells are subsequently infected with the adenovirus Ad5. Vectors can be purified from cell lysates using methods known in the art (e.g., such as cesium chloride density gradient ultracentrifugation) and are validated to ensure that they are free of detectable replication-competent AAV or adenovirus (e.g., by a cytopathic effect bioassay). AAV titer may be determined by quantitative PCR with virus DNA samples prepared after digestion with proteinase K. Preferably, vector titers produced by such a method are approximately $5 \times 10^{12}$ to $1 \times 10^{13}$ DNase resistant particles per ml.

In other aspects, retroviral vectors are used. Retroviruses are a class of integrative viruses which replicate using a virus-encoded reverse transcriptase, to replicate the viral RNA genome into double stranded DNA which is integrated into chromosomal DNA of the infected cells (e.g., target cells). Such vectors include those derived from murine leukemia viruses, especially Moloney (Gilboa, et al., 1988, *Adv. Exp. Med. Biol.* 241: 29) or Friend's FB29 strains (WO 95/01447). Generally, a retroviral vector is deleted of all or part of the viral genes gag, pol and env and retains 5' and 3' LTRs and an encapsidation sequence. These elements may be modified to increase expression level or stability of the retroviral vector. Such modifications include the replacement of the retroviral encapsidation sequence by one of a retrotransposon such as VL30 (see, e.g., U.S. Pat. No. 5,747,323). Preferably, the polynucleotide of interest is inserted downstream of the encapsidation sequence, preferably in opposite direction relative to the retroviral genome. Cell specific targeting may be achieved by the conjugation of antibodies or antibody fragments to the retroviral envelope protein as is know in the art.

Retroviral particles are prepared in the presence of a helper virus or in an appropriate complementation (packaging) cell line which contains integrated into its genome the retroviral genes for which the retroviral vector is defective (e.g. gag/pol and env). Such cell lines are described in the prior art (Miller and Rosman, 1989, *BioTechniques* 7: 980; Danos and Mulligan, 1988, *Proc. Natl. Acad. Sci. USA* 85: 6460; Markowitz, et al., 1988, *Virol.* 167: 400). The product of the env gene is responsible for the binding of the viral particle to the viral receptors present on the surface of the target cell and, therefore determines the host range of the retroviral particle. in the context of the invention, it is advantageous to use a packaging cell line, such as the PA317 cells (ATCC CRL 9078) or 293EI6 (WO97/35996) containing an amphotropic envelope protein, to allow infection of human and other species' target cells. The retroviral particles are preferably recovered from the culture supernatant and may optionally be further purified according to standard techniques (e.g. chromatography, ultracentrifugation).

Other suitable viruses include poxviruses. The genome of several members of poxyiridae has been mapped and sequenced. A poxyiral vector may be obtained from any member of the poxyiridae, in particular canarypox, fowlpox and vaccinia virus. Suitable vaccinia viruses include, but are not limited to, the Copenhagen strain (Goebel, et al., 1990, *Virol.* 179: 247-266; Johnson, et al., 1993, *Virol.* 196: 381-401), the Wyeth strain and the modified Ankara (MVA) strain (Antoine, et al., 1998, *Virol.* 244: 365-396). The general conditions for constructing a vaccinia virus vector are known in the art (see, e.g., EP 83 286 and EP 206 920; Mayr et al., 1975, *Infection* 3: 6-14; Sutter and Moss, 1992, *Proc. Natl. Acad. Sci. USA* 89: 10847-10851). Preferably, the polynucleotide of interest is inserted within a non-essential locus such as the nOD7coding intergenic regions or any gene for which inactivation or deletion does not significantly impair viral growth and replication.

Poxyiral particles are prepared as described in the art (Piccini, et al., 1987, *Methods of Enzymology* 153: 545-563; U.S. Pat. No. 4,769,330; U.S. Pat. No. 4,772,848; U.S. Pat. No. 4,603,112; U.S. Pat. No. 5,100,587 and U.S. Pat. No. 5,179,993). Generally, a donor plasmid is constructed, amplified by growth in *E. coli* and isolated by conventional procedures. Then, it is introduced into a suitable cell culture (e.g. chicken embryo fibroblasts) together with a poxvirus genome, to produce, by homologous recombination, poxyiral particles. These can be recovered from the culture supernatant or from the cultured cells after a lysis step (e.g., chemical lysis, freezing/thawing, osmotic shock, sonication and the like). Consecutive rounds of plaque purification can be used to remove contaminating wild type virus. Viral particles can then be purified using the techniques known in the art (e.g., chromatographic methods or ultracentrifugation on cesium chloride or sucrose gradients).

The use of vaccinia as a live virus vaccine in the global campaign to eradicate smallpox made vaccinia an obvious choice for development as a live recombinant vaccine vector. Live recombinant vaccinia viruses expressing close to 100 different foreign proteins have been reported, and a number of these are effective experimental vaccines (reviewed by Moss and Flexner, 1987). Vaccinia is particularly versatile as an expression vector because of its large genomic size, capability of accepting at least 25,000 base pairs of foreign DNA, and its ability to infect most eukaryotic cell types, including insect cells (ibid.). Unlike other DNA viruses, poxviruses replicate exclusively in the cytoplasm of infected cells, reducing the possibility of genetic exchange of recombinant viral DNA with the host chromosome. Recombinant vaccinia vectors have been shown to properly process and express proteins from a variety of sources including man, other mammals, parasites, RNA and DNA viruses, bacteria and bacteriophage.

The virus is capable of infecting most mammals, making it a useful vector for studying a broad range of human and animal diseases. The expression of DNA encoding a foreign protein is controlled by host virus regulatory elements, including upstream promoter sequences and, where necessary, RNA processing signals. Insertion of foreign DNA into nonessential regions of the vaccinia virus genome has been carried out by homologous recombination (Panicali, et al., *Proc. Nat'l. Acad. Sci, USA,* 79: 4927, 1982; Mackett, et al., *Proc. Nat'l. Acad. Sci. USA,* 79: 7415, 1982).

Expression of foreign genes within the DNA may occur because of transcriptional regulatory elements at or near the site of insertion or by more precise genetic engineering. Plasmid vectors that greatly facilitate insertion and expression of foreign genes have been constructed (Mackett, et al., *J. Virol,* 49: 857, 1982). These vectors contain an expression site, composed of a vaccinia transcriptional promoter and one or more unique restriction endonuclease sites for insertion of the foreign coding sequence flanked by DNA from a nonessential region of the vaccinia genome. The choice of promoter determines both the time (e.g., early or late) and level of expression, whereas the flanking DNA sequence determines the site of homologous recombination.

Only about one in a thousand virus particles produced by this procedure is a recombinant. Although recombinant virus plaques can be identified by DNA hybridization, efficient selection procedures have been developed. By using segments of nonessential vaccinia virus thymidine kinase (TK) gene as flanking sequences, the foreign gene recombines into the TK locus and by insertion inactivates the TK gene. Selection of TK virus is achieved by carrying out the virus plaque assay in TK cells in the presents of 5-bromodeoxyuridine. Phosphorylation of the nucleoside analogue and consequent lethal incorporation into viral DNA occurs only in cells infected with TK.sup.+ parental virus. Depending on the efficiency of the transfection and recombination, up to 80 of the plaques are desired recombinants, and the rest are spontaneous TK mutants.

Plasmid vectors that contain the *E. coli* β-galactosidase gene, as well as an expression site for a second gene, permit an alternative method of distinguishing recombinant from parental virus (Chakrabarti, et al., *Mol. Cell. Biol.,* 5: 3403, 1985). Plaques formed by such recombinants can be positively identified by the blue color that forms upon addition of an appropriate indicator. By combining both TK selection and beta-galactosidase expression, recombinant virus is readily and quickly isolated. The recombinants are then amplified by propagation in suitable cell lines and expression of the inserted gene is checked by appropriate enzymological, immunological or physical procedures.

An upper limit to the amount of genetic information that can be added to the vaccinia virus genome is not yet known. However, the addition of nearly 25,000 base pairs of foreign DNA had no apparent deleterious effect on virus yield (Smith, et al., Gene, 25:21, 1983). Were it necessary, large segments of the vaccinia virus genome could be deleted to provide additional capacity (Moss, et al., *J. Virol.* 40: 387, 1981).

Viral capsid molecules may include targeting moieties to facilitate targeting and/or entry into cells. Suitable targeting molecules, include, but are not limited to: chemical conjugates, lipids, glycolipids, hormones, sugars, polymers (e.g. PEG, polylysine, PEI and the like), peptides, polypeptides (see, e.g., WO 94/40958), vitamins, antigens, lectins, antibodies and fragments thereof. Preferably, such targeting molecules recognize and bind to cell-specific markers, tissue-specific markers, cellular receptors, viral antigens, antigenic epitopes or tumor-associated markers.

A composition based on viral particles may be formulated in the form of doses of between 10 and $10^{14}$ i.u. (infectious units), and preferably, between 10 and $10^{11}$ i.u. The titer may be determined by conventional techniques. The doses of nucleic acid delivery vector are preferably comprised between 0.01 and 10 mg/kg, more especially between 0.1 and 2 mg/kg.

Cell-Based Delivery Vehicles

The nucleic acid vectors according to the invention can be delivered to target cells by means of other cells ("delivery cells) which comprise the vectors. Methods for introducing vectors into cells are known in the art and include microinjection of DNA into the nucleus of a cell (Capechi, et al., 1980, *Cell* 22: 479-488); transfection with CaP0$_4$ (Chen and Okayama, 1987, *Mol. Cell Biol.* 7: 2745 2752), electroporation (Chu, et al., 1987, *Nucleic Acid Res.* 15: 1311-1326); lipofection/liposome fusion (Feigner, et al., 1987, *Proc. Natl. Acad. Sci. USA* 84: 7413-7417) and particle bombardment (Yang, et al., 1990, *Proc. Natl. Acad. Sci. USA* 87: 9568-9572). Suitable cells include autologous and non-autologous cells, and may include xenogenic cells. Delivery cells may be induced to deliver their contents to the target cells by inducing their death (e.g., by providing inducible suicide genes to these cells).

Accessory Molecules

The compositions according to the invention may comprise one or more accessory molecules for facilitating the introduction of a nucleic acid delivery vector into a cell and/or for enhancing a particular therapeutic effect.

In addition, the composition according to the present invention may include one or more stabilizing substance(s), such as lipids, nuclease inhibitors, hydrogels, hyaluronidase (WO 98/53853), collagenase, polymers, chelating agents (EP 890362), in order to inhibit degradation within the animal/human body and/or improve transfection/infection of the vector into a target cell. Such substances may be used alone or in combination (e.g., cationic and neutral lipids).

It has also been shown that adenovirus proteins are capable of destabilizing endosomes and enhancing the uptake of DNA into cells. The mixture of adenoviruses to solutions containing a lipid-complexed DNA vector or the binding of DNA to polylysine covalently attached to adenoviruses using protein cross-linking agents may substantially improve the uptake and expression of a nucleic acid delivery vector (see, e.g., Curiel, et al., 1992, *Am. I. Respir. Cell. Mol. Biol.* 6: 247-252).

Host Cells

Nucleic acid vectors according to the invention can be expressed in a variety of host cell, including, but not limited to: prokaryotic cells (e.g., *E. coli, Staphylococcus* sp., *Bacillus* sp.); yeast cells (e.g., *Saccharomyces* sp.); insect cells; nematode cells; plant cells; amphibian cells (e.g., Xenopus); avian cells; and mammalian cells (e.g., human cells, mouse cells, mammalian cell lines, primary cultured mammalian cells, such as from dissected tissues).

The molecules can be expressed in host cells isolated from an organism, host cells which are part of an organism, or host cells which are introduced into an organism. In one aspect, fusion molecules are expressed in host cells in vitro, e.g., in culture. In another aspect, fusion molecules are expressed in a transgenic organism (e.g., a transgenic mouse, rat, rabbit, pig, primate, etc.) that comprises somatic and/or germline cells comprising nucleic acids encoding the fusion molecules. Methods for constructing transgenic animals are well known in the art and are routine.

Nucleic acid vectors also can be introduced into cells in vitro, and the cells (e.g., such as stem cells, hematopoietic cells, lymphocytes, and the like) can be introduced into the host organism. The cells may be heterologous or autologous with respect to the host organism. For example, cells can be obtained from the host organism, nucleic acid vectors introduced into the cells in vitro, and then reintroduced into the host organism.

Antigen Presenting Cells

In a preferred aspect of the invention, a nucleic acid delivery vehicle such as described above is introduced into a natural or engineered antigen presenting cell.

The term "antigen presenting cell" (APC) as used herein intends any cell which presents on its surface an antigen in association with a major histocompatibility complex molecule, preferably a class II molecule, or portion thereof. Examples of suitable APCs are discussed in detail below and include, but are not limited to, whole cells such as macrophages, dendritic cells, B cells, hybrid APCs, and foster antigen presenting cells. Methods of making hybrid APCs are described and known in the art.

Dendritic cells (DCs) are potent antigen-presenting cells. It has been shown that DCs provide all the signals required for T cell activation and proliferation. These signals can be categorized into two types. The first type, which gives specificity to the immune response, is mediated through interaction between the T-cell receptor/CD3 ("TCR/CD3") complex and an antigenic peptide presented by a major histocompatibility complex ("MHC" defined above) class I or II protein on the surface of APCs. This interaction is necessary, but not sufficient, for T cell activation to occur. In fact, without the second type of signals, the first type of signals can result in T cell anergy. The second type of signals, called co-stimulatory signals, is neither antigen-specific nor MHC-restricted, and can lead to a full proliferation response of T cells and induction of T cell effector functions in the presence of the first type of signals.

Several molecules have been shown to enhance co-stimulatory activity. These include, but are not limited to, heat stable antigen (HSA), chondroitin sulfate-modified MHC invariant chain (Ii-CS), intracellular adhesion molecule I (ICAM-1), and B7 co-stimulatory molecule on the surface of APCs and its counter-receptor CD28 or CTLA-4 on T cells.

Other important co-stimulatory molecules are CD40, CD54, CD80, CD86. As used herein, the term "co-stimulatory molecule" encompasses any single molecule or combination of molecules which, when acting together with a peptide/MHC complex bound by a TCR on the surface of a T cell, provides a co-stimulatory effect which achieves activation of the T cell that binds the peptide. The term thus encompasses B7, or other co-stimulatory molecule(s) on an APC, fragments thereof (alone, complexed with another molecule(s), or as part of a fusion protein) which, together with peptide/MHC complex, binds to a cognate ligand and result in activation of the T cell when the TCR on the surface of the T cell specifically binds the peptide. Co-stimulatory molecules are commercially available from a variety of sources, including, for example, Beckman Coulter.

In one aspect of the invention, the method described in Romani et al., *J. Immunol. Methods* 196: 135-151, 1996, and Bender et al, *J. Immunol. Methods* 196: 121-135, 1996, are used to generate both immature and mature dendritic cells from the peripheral blood mononuclear cells (PBMCs) of a mammal, such as a murine, simian or human. Briefly, isolated PBMCs are pre-treated to deplete T- and B-cells by means of an immunomagnetic technique. Lymphocyte-depleted PBMC are then cultured for in RPMI medium 9 e.g., about 7 days), supplemented with human plasma (preferably autologous plasma) and GM-CSF/IL-4, to generate dendritic cells. Dendritic cells are nonadherent when compared to their monocyte progenitors. Thus, on approximately day 7, nonadherent cells are harvested for further processing.

The dendritic cells derived from PBMC in the presence of GM-CSF and IL-4 are immature, in that they can lost the nonadherence property and revert back to macrophage cell fate if the cytokine stimuli are removed from the culture. The dendritic cells in an immature state are very effective in processing native protein antigens for the MHC class II restricted pathway (Romani, et al., J. Exp. Med. 169:1169, 1989). Further maturation of cultured dendritic cells is accomplished by culturing for 3 days in a macrophage-conditioned medium (CM), which contains the necessary maturation factors. Mature dendritic cells are less able to capture new proteins for presentation but are much better at stimulating resting T cells (both CD4 and CD8) to grow and differentiate.

Mature dendritic cells can be identified by their change in morphology, such as the formation of more motile cytoplasmic processes; by their nonadherence; by the presence of at least one of the following markers: CD83, CD68, HLA-DR or CD86; or by the loss of Fc receptors such as CD 115 (reviewed in Steinman, *Annu. Rev. Immunol.* 9: 271, 1991). Mature dendritic cells can be collected and analyzed using typical cytofluorography and cell sorting techniques and devices, such as FACScan and FACStar. Primary antibodies used for flow cytometry are those specific to cell surface antigens of mature dendritic cells and are commercially available. Secondary antibodies can be biotinylated Igs followed by FITC- or PE-conjugated streptavidin.

Alternatively, others have reported that a method for upregulating (activating) dendritic cells and converting monocytes to an activated dendritic cell phenotype. This method involves the addition of calcium ionophore to the culture media convert monocytes into activated dendritic cells. Adding the calcium 21 ionophore A23187, for example, at the beginning of a 24-48 hour culture period resulted in uniform activation and dendritic cell phenotypic conversion of the pooled "monocyte plus DC" fractions: characteristically, the activated population becomes uniformly CD 14 (Leu M3) negative, and upregulates HLA-DR, HLA-DQ, ICAM-1,137.1, and 137.2. Furthermore, this activated bulk population functions as well on a small numbers basis as a further purified. Specific combination(s) of cytokines have been used successfully to amplify (or partially substitute) for the activation/conversion achieved with calcium ionophore: these cytokines include but are not limited to G-CSF, GM-CSF, IL-2, and IL-4. Each cytokine when given alone is inadequate for optimal upregulation.

The second approach for isolating APCs is to collect the relatively large numbers of precommitted APCs already circulating in the blood. Previous techniques for isolating committed APCs from human peripheral blood have involved combinations of physical procedures such as metrizamide gradients and adherence/nonadherence steps (Freudenthal et al. *PNAS* 87: 7698-7702, 1990); Percoll gradient separations (Mehta-Damani, et al., *J. Immunol.* 153: 996-1003, 1994); and fluorescence activated cell sorting techniques (Thomas et al., *J. Immunol.* 151: 6840-52, 1993).

It should be obvious to those of skill in the art that there are many methods routine in the art for isolating professional antigen presenting cells (or their precursors) and that such methods and others which may be developed are not limiting and are encompassed within the scope of the invention.

In one embodiment, the APCs and therefore the cells presenting one or more antigens are autologous. In another embodiment, the APCs presenting the antigen are allogeneic, i.e., derived from a different subject.

As discussed above, nucleic acids encoding chimeric molecules can be introduced into APCs using the methods described above or others known in the art, including, but not limited to, transfection, electroporation, fusion, microinjection, viral-based delivery, or cell based delivery. Arthur et al., *Cancer Gene Therapy* 4(1): 17-25, 1997, reports a comparison of gene transfer methods in human dendritic cells.

Known, partial and putative human leukocyte antigen (HLA), the genetic designation for the human MHC, amino acid and nucleotide sequences, including the consensus sequence, are published (see, e.g., Zemmour and Parham, *Immunogenetics* 33: 310-320, 1991), and cell lines expressing HLA variants are known and generally available as well, many from the American Type Culture Collection ("ATCC"). Therefore, using PCR, MHC class II-encoding nucleotide sequences are readily operatively linked to an expression vector of this invention that is then used to transform an appropriate cell for expression therein.

Professional APCs can be used, such as macrophages, B cells, monocytes, dendritic cells, and Langerhans cells. These are collected from the blood or tissue of 1) an autologous donor; 2) a heterologous donor having a different HLA specificity then the host to be treated; or 3) from a xenogeneic donor of a different species using standard procedures (Coligan, et. al., *Current Protocols in Immunology*, sections 3 and 14, 1994). The cells may be isolated from a normal host or a patient having an infectious disease, cancer, autoimmune disease, or allergy.

Professional APCs may be obtained from the peripheral blood using leukopheresis and "FICOLL/HYPAQUE" density gradient centrifugation (stepwise centrifugation through Ficoll and discontinuous Percoll density gradients). Procedures are utilized which avoid the exposure of the APCs to antigens which could be internalized by the APCs, leading to activation of T cells not specific for the antigens of interest.

Cells which are not naturally antigen presenting can be engineered to be antigen presenting by introducing sequences encoding appropriate molecules. For example, nucleic acid sequences encoding MHC class II molecules, accessory molecules, co-stimulatory molecules and antigen processing assisting molecules can be introduced after direct synthesis, cloning, purification of DNA from cells containing such genes, and the like. One expedient means to obtain genes for encoding the molecules used in the compositions and methods described herein is by polymerase chain reaction (PCR)

amplification on selected nucleic acid templates with selected oligonucleotide primer pairs. For example, epithelial cells, endothelial cells, tumor cells, fibroblasts, activated T cells, eosinophils, keratinocytes, astrocytes, microglial cells, thymic cortical epithelial cells, Schwann cells, retinal pigment epithelial cells, myoblasts, vascular smooth muscle cells, chondrocytes, enterocytes, thyrocytes and kidney tubule cells can be used. These may be primary cells recently explanted from a host and not extensively passaged in cell culture to form an established cell line, or established cell lines that are relatively homogeneous and capable of proliferating for many generations or indefinitely.

Cells that are not professional APCs are isolated from any tissue of an autologous donor; a heterologous donor or a xenogeneic donor, where they reside using a variety of known separation methods (Darling, *Animal Cells: Culture and Media*. J. Wiley, New York, 1994; Freshney, Culture of Animal Cells. Alan R. Liss, Inc., New York, 1987). Non-autologous cells, e.g., heterologous or xenogeneic cells, can be engineered ex vivo to express HLA class I and class II molecules that match known human HLA specificities. These cells can then be introduced into a human subject matching the HLA specificity of the engineered cells. The cells are further engineered ex vivo to express one or more chimeric vaccines according to the invention.

The engineered cells are maintained in cell culture by standard cell culture methods (Darling, Animal Cells: Culture and Media". J. Wiley, New York, 1994; Freshney, Culture of Animal Cells". Alan R. Liss, Inc., New York, 1987). Cell lines for use in the present invention are obtained from a variety of sources (e.g., ATCC Catalogue of Cell Lines & Hybidomas, American Type Culture Collection, 8th edition, 1995), or are produced using standard methods (Freshney, Culture of Immortalized Cells, Wiley-Liss, New York, 1996). Non-transformed cell lines are preferred for use in human subjects.

In one aspect, $CD34^+$ precursors that are differentiating under the influence of GM-CSF into dendritic cells are obtained from the body of a subject and nucleic acids encoding chimeric vaccines according to the invention are introduced into the cells, which are then re-injected into the subject. Utilizing the construct containing antigenic sequences linked to an endosomal/lysosomal targeting signal (and preferably comprising a LAMP-like lumenal polypeptide) will enhance the association of peptides derived from a particular antigen with MHC class II molecules on the transduced antigen presenting cells, resulting in significantly more potent systemic T cell dependent immune responses. While the antigen presenting cells transfected in this strategy are preferably autologous cells, any MHC class II cells that effectively present antigen in the host may be used as described above.

Peptide Vaccines

Also within the scope of this invention are vaccines containing cell-free peptide immunogens, where the immunogen contains an antigen domain and sequences of a lysosomal membrane polypeptide (e.g., such as a LAMP polypeptide or a homolog, ortholog, variant, or modified version thereof) or sequences of an endocytic receptor for targeting and trafficking the antigen to an endosomal/lysosomal compartment or lysosome-related organelle for binding to an MHC class II molecule or for delivery to another compartment/organelle for binding to an MHC class II molecule. Preferably, the antigen is processed within the compartment/organelle (or subsequent compartment/organelle to which it is delivered) to generate an epitope bound to an MHC class II molecule capable of modulating an immune response.

The chimeric vaccine may also comprise a transmembrane region and/or cytoplasmic tail with lysosomal targeting region (preferably from a LAMP polypeptide), and/or di-leucine domain, Tyr motif, MR6 domain, proline rich domain, and/or Ser-Val-Val domain. The chimeric vaccine also may be bound in a membranous structure to facilitate its administration to the body of an organism. For example, the chimeric vaccine may beincorporated into liposomes, as described in U.S. Pat. No. 4,448,765.

When a protein or polypeptide is to be used as an immunogen, it may be produced by expression of any one or more of the DNA constructs described above in a recombinant cell or it may be prepared by chemical synthesis. For example, the Merrifield technique (*Journal of American Chemical Society*, vol. 85, pp. 2149-2154, 1968), can be used.

Administration

Vaccine material according to this invention may contain the immune stimulatory constructs described above or may be recombinant microorganisms, or antigen presenting cells which express the immune stimulatory constructs. Preparation of compositions containing vaccine material according to this invention and administration of such compositions for immunization of individuals are accomplished according to principles of immunization that are well known to those skilled in the art.

Large quantities of these materials may be obtained by culturing recombinant or transformed cells containing replicons that express the chimeric DNA described above. Culturing methods are well-known to those skilled in the art and are taught in one or more of the documents cited above. The vaccine material is generally produced by culture of recombinant or transformed cells and formulated in a pharmacologically acceptable solution or suspension, which is usually a physiologically-compatible aqueous solution, or in coated tablets, tablets, capsules, suppositories or ampules, as described in the art, for example in U.S. Pat. No. 4,446,128, incorporated herein by reference. Administration may be any suitable route, including oral, rectal, intranasal or by injection where injection may be, for example, transdermal, subcutaneous, intramuscular or intravenous.

The vaccine composition is administered to a mammal in an amount sufficient to induce an immune response in the mammal. A minimum preferred amount for administration is the amount required to elicit antibody formation to a concentration at least 4 times that which existed prior to administration. A typical initial dose for administration would be 10-5000 micrograms when administered intravenously, intramuscularly or subcutaneously, or $10^5$ to $10^{11}$ plaque forming units of a recombinant vector, although this amount may be adjusted by a clinician doing the administration as commonly occurs in the administration of vaccines and other agents which induce immune responses. A single administration may usually be sufficient to induce immunity, but multiple administrations may be carried out to assure or boost the response.

Vaccines may be tested initially in a non-human mammal (e.g., a mouse or primate). For example, assays of the immune responses of inoculated mice can be used to demonstrate greater antibody, T cell proliferation, and cytotoxic T cell responses to the lysosome-targeted chimeric proteins than to wild type antigen. Chimeric proteins can be evaluated in Rhesus monkeys to determine whether a DNA vaccine formulation that is highly effective in mice will also elicit an appropriate monkey immune response. In one aspect, each monkey receives a total of 5 mg DNA per immunization, delivered IM and divided between 2 sites, with immunizations at day 0 and at weeks 4, 8, and 20, with an additional doses optional. Antibody responses, ADCC, $CD4^+$ and $CD8^+$ T-cell cytokine production, $CD4^+$ and $CD8^+$ T-cell antigen-specific cytokine staining can be measured to monitor immune responses to the vaccine.

Further description of suitable methods of formulation and administration according to this invention may be found in U.S. Pat. No. 4,454,116 (constructs), U.S. Pat. No. 4,681,762 (recombinant bacteria), and U.S. Pat. Nos. 4,592,002 and 4,920,209 (recombinant viruses).

Immune Tolerance and Autoimmunity

Many auto-immune diseases show a correlation with certain MHC class II haplotypes and are associated with aberrant auto-antibody production, suggesting that the generation of self-reactive MHC class II restricted $CD4^+$ T cells is an important pathogenetic step. Given that $CD4^+$ cells can, under certain circumstances, be inactivated or anergized by engagement of their T cell receptor in the absence of a second signal (such as the co-engagement of CD28 by its ligand B7), it follows that the efficient presentation of an MHC class II restricted antigen on an MHC class II cell that did not display the appropriate second signal would represent an effective toleragen. The generation of this tolerance or inactivation of certain $CD4^+$ T cells could be used to turn off aberrant immune responses in auto-immune diseases.

In the embodiment of this principle, a poor antigen presenting cell (that did not express any co-stimulatory signals) would either be induced to express MHC class II or would be transfected with the appropriate MHC class II genes. This cell would then be additionally transduced with the auto-antigen of interest, such as the acetylcholine receptor in the case of myaesthenia gravis, linked to the endosomal/lysosomal targeting signal. Injection of these cells into the host would result in turning off T cell responses against the antigen, based on the efficient presentation of peptide sequences on MHC class II molecules to T cell receptors on $CD4^+$ T cells in the absence of the appropriate co-stimulatory signals (signals that are provided by effective antigen present cells).

Cancer Immunotherapy

Candidates for Prevention and Treatment

Candidates for cancer immunotherapy would be any patient with a cancer possessing a defined and identified tumor specific antigen whose gene can be cloned and modified by the LAMP lysosomal/endosomal targeting sequences as described herein. Examples include patients with documented Epstein-Barr virus associated lymphomas, patients with HPV associated cervical carcinomas, patients with chronic HCV, or patients with a defined re-arrangement or mutation in an oncogene or tumor suppressor gene. It is envisioned that therapy with a vaccine incorporating the tumor antigen linked to the endosomal/lysosomal trafficking and targeting sequences in a viral vaccine could be utilized at any period during the course of the individual's cancer, once it is identified. It is also possible that in high risk patients, vaccination in order to prevent the subsequent emergence of a cancer with a defined tumor specific antigen could be performed.

Procedure for Therapy

In one embodiment, recombinant viral vaccine containing the antigen linked with the lysosomal/endosomal trafficking and targeting sequence incorporated into a viral vaccine such as vaccinia, would be produced in large quantities as described above and would be injected into the patient at any suitable time during the course of their malignancy. Preferably, the vaccine would be injected at a stage when the tumor burden was low. In an alternative embodiment in which this construct is introduced into the individual's antigen presenting cells, precursors to the antigen presenting cells or mature antigen presenting cells are drawn either from the individual's bone marrow or peripheral blood by vena puncture. These cells are established in culture followed by transduction with the chimeric construct. Once transduction had occurred, these antigen presenting cells are injected back into the patient.

In a particularly preferred embodiment, the invention provides a method of treatment for a cancer patient having low tumor burden, such as early in the disease, after resection of a neoplastic tumor, or when the burden of tumor cells is otherwise reduced. In this method, once a tumor-specific cell surface antigen characteristic of the patient's tumor has been identified, a cell population containing autologous stem cells capable of differentiation into antigen presenting cells which will express MHC class II molecules is obtained from the patient. These cells are cultured and transformed by introducing a heterologous or chimeric DNA molecule which encodes a protein containing at least one epitope of the tumor-specific antigen found on the cells of the patient's tumor and a lumenal trafficking domain of a lysosome associated membrane polypeptide (e.g., LAMP polypeptide, homolog, ortholog, variant, or modified form thereof) or the lumenal trafficking domain of an endocytic receptor, and a cytoplasmic targeting domain of a LAMP polypeptide, homolog, ortholog, variant, or modified form thereof, or of an endocytic receptor for targeting the antigen to an endosomal/lysosomal compartment or lysosome-related organelle and for association with an MHC class II molecule either within the compartment/organelle or within another compartment/organelle to which the antigen is delivered. Such chimeric DNA molecules can encode additional domain sequences as described above (e.g., sequences encoding transmembrane domains; signal sequences, cytoplasmic domains for targeting to an endosomal/lysosomal compartment or lysosome-related organelles, di-leucine domains, Tyr motif domains, proline rich domains, Ser-Val-Val domains, and the like).

The transfected stem cell population is then reintroduced into the patient, where the stem cells differentiate into antigen presenting cells which express MHC class II molecules complexed with $T_h$ epitopes from the tumor-specific antigen. The immune response to the tumor-specific antigen will be enhanced by enhanced stimulation of the helper T cell population.

More generally, in one embodiment, this invention provides a vaccine composition for modulating an immune response in a mammal to an antigen (i.e., stimulating, enhancing, or reducing such a response). Preferably, the composition comprises a vaccine vector, wherein the vector contains a chimeric DNA segment which encodes a protein containing at least one epitope of the tumor-specific antigen found on the cells of the patient's tumor and a lumenal trafficking domain of a lysosome associated membrane polypeptide (e.g., LAMP polypeptide, homolog, ortholog, variant, or modified form thereof) or the lumenal trafficking domain of an endocytic receptor, and a targeting domain, such as the cytoplasmic targeting domain of a LAMP polypeptide, homolog, ortholog, variant, or modified form thereof, or of an endocytic receptor, for targeting the antigen to an endosomal/lysosomal compartment or lysosome-related organelle and for association with an MHC class II molecule either within the compartment/organelle or within another compartment/organelle to which the antigen is delivered. Such chimeric DNA molecules can encode additional domain sequences as described above (e.g., sequences encoding transmembrane domains; signal sequences, cytoplasmic domains for targeting to an endosomal/lysosomal compartment or lysosome-related organelles, di-leucine domains, Tyr motif domains, proline rich domains, Ser-Val-Val domains, and the like). Kits The invention further comprises kits to facilitate performing the methods described herein. In one aspect, a kit comprises a nucleic acid vector as described above and a cell for receiving the vector. The kit may additionally comprise one or more nucleic acids for engineering the cell into a professional APC. In one aspect, however, the cell is a professional APC. The cell may or may not express co-stimulatory molecules. In a preferred aspect, when the cell does not express co-stimulatory molecules, the antigen encoded by the vector is an autoantigen. In another aspect, a panel of cells is provided expressing different MHC molecules (e.g., known to be expressed in human beings). In a further aspect, the kit comprises reagents to facilitate entry of the vectors into a cell (e.g., lipid-based formulations, viral packaging materials, cells, and the like). In still a further aspect, one or more T cell lines specific for the antigen encoded by the vector is provided, to verify the ability of the vector to elicit, modulate, or enhance an immune response.

EXAMPLES

The invention will now be further illustrated with reference to the following examples. It will be appreciated that what follows is by way of example only and that modifications to detail may be made while still falling within the scope of the invention.

Example 1

High Level Expression HIV-1 Gag In Vitro by Plasmids Containing Antigen Inserted into the Full Lamp Sequences and the Adeno Associated Virus Inverted Terminal Repeat Sequences A number of different nucleic acid constructs were constructed encoding chimeric vaccines.

A plasmid capable of eliciting a high level of Gag expression as a fusion protein with LAMP in transfected cells is shown in FIG. 1. Gag expression by this plasmid is compared to that of a number of other plasmid constructs in the figure. For example, Plasmid 1 comprises the wild type [HIV-1] Gag gene in the pcDNA3.1 (Invitrogen) vector backbone. Plasmid 2 comprises a gag chimera containing LAMP signal sequence, transmembrane and cytoplasmic domains, in pcDNA3.1. Plasmid 3 comprises a chimera with Gag inserted between the lumenal and transmembrane/cytoplasmic domains of the complete LAMP cDNA in pcDNA3.1. Plasmid 4 shows HIVGagΔINS[15] containing mutations of the Gag inhibitory sequences in pcDNA3.1. Plasmid 5 comprises HIVGagΔINS[15] with the LAMP signal sequence, transmembrane and cytoplasmic domains pcDNA3.1. Plasmid 6 comprises p43 vector backbone containing the AAV-ITRs and encoding wild type Gag. Plasmid 7 shows a p43 vector backbone containing gag inserted into the full length LAMP as in plasmid 3.

The Data show, as expected, that the control plasmid (#1) and the one containing the Gag/LAMP transmembrane and cytoplasmic tail chimera (#2) did not show significant protein expression. In contrast, this experiment resulted in the novel finding of strong Gag expression with the gag gene included within the full LAMP gene (#3). The amount of Gag protein expressed was notably greater than that of the plasmid encoding Gag with the mutated INS sequences alone (#4) or as a chimera with the LAMP transmembrane and cytoplasmic tail (#5). A further, and even more remarkable finding was the relatively great Gag protein expression of the p43 plasmid containing the AAV ITR sequences and the gag gene incorporated in the complete LAMP sequence (#7). The same p43 plasmid construct but without the LAMP sequences showed very little Gag expression (#6). Similar protein expression as observed in with plasmid #7 in this experiment was observed after transfection of several cell lines (COS, 293T, 3T3).

Thus, inserting HIV Gag near the extracellular side of the transmembrane domain of the full-length mouse LAMP-1 results in a much greater expression of HIV Gag as a fusion protein with LAMP as compared to the wild type Gag or Gag modified only with the LAMP endoplasmic reticulum translocation signal sequence, and Gag expression that was greater even than that of the plasmid encoding Gag with the mutated INS sequences. In addition, Gag expression of our new HIV Gag-LAMP chimera was remarkably further enhanced by a plasmid DNA vector containing non-translated sequences of the inverted terminal repeats (ITRs) of the adeno-associated virus (AAV) (p43 vector).

Example 2

Evaluation of the Immune Response of Mice to Plasmids Encoding a Complete LAMP/HIV-1 Gag Chimera Protein High level expression in transfected cells of Gag protein as a chimera of approximately 200 kDa (assayed by anti-Gag antibodies) was found to result from insertion of the HIV-1 p55Gag sequence downstream of the coding sequence of the LAMP lumenal domain (1113 bp) (FIG. 7E construct #3). Moreover Gag expression was further markedly amplified by including AAV ITRs into the expression vector. Approximately 40-fold greater expression was observed for this construct than for a LAMP/Gag construct without such sequences as determined by densitometry. This expression was 200-fold greater than the expression of wild type Gag (FIG. 7E construct #7). There was minimal Gag protein expression in transfected cells with plasmids that lacked the LAMP lumenal domain, even in plasmids containing the ITR (FIG. 7E, constructs #1, 2, 6). Thus, the high level expression of Gag required the lumenal domain of LAMP.

The cellular localization of LAMP/Gag was analyzed by transfecting the mouse fibroblast cell line DCEK.ICAM.Hi7, which expresses MHC class II I-Ek molecules, ICAM-1, and B7-1, and can present pre-processed peptides to naïve CD4 T cells. Class II molecules of this cell line have been shown to colocalize with LAMP-1. Monoclonal anti-Gag staining of DCEK cells transfected with wild type Gag revealed a diffuse cytoplasmic distribution of the wild type protein. In contrast, DCEK transfected with the LAMP/Gag construct and stained with anti-Gag showed a striking colocalization of the LAMP/Gag chimera with MHC II in several highly labeled vesicles.

The ability of the chimeric proteins to modulate an immune response was also evaluated. Groups of six mice were immunized with 50 μg of DNA at the base of the tail on days 0, 30, 60 and 90 with the following plasmid constructs as follows. Blood samples were obtained on days—1, 29, 59, and 89, and half of the mice sacrificed on days 70 and 100. The effects of various constructs were examined: 1) pcDNA wild type Gag; 2) pcDNA LAMP signal sequence/Gag/LAMP transmembrane and cytoplasmic domains; 3) pcDNA lumenal domain of LAMP/Gag/LAMP transmembrane and cytoplasmic domains; 4) pcDNA Gag mutated inhibitory sequences; 5) pcDNA signal sequence/mutated inhibitory sequences/LAMP transmembrane and cytoplasmic domains; 6) p43 (AAV-ITR) wild type Gag; and 7) p43 (AAV-ITR) lumenal domain of LAMP/Gag/LAMP transmembrane and cytoplasmic domains.

The HIV specific antibody response in each mouse was assayed at 1:100 dilution of the plasma collected on day 59, after two immunizations. The data are shown as the average of these individual assays (n=5) (FIG. 2). The Gag gene encoded in the full length LAMP cDNA, particularly that contained in the p43 vector, elicited a much stronger immune response than did any of the other constructs. The GagINS constructs elicited lesser responses whereas there was no response to any of the wild type Gag gene constructs. The combination of the full-length LAMP/gag chimera and the AAV plasmid are remarkably more immunogenic than any of the conventional DNA vaccine constructs.

The pooled sera collected after the second to fourth immunizations, days 59, 89, and 119, were also tested for the titer of the antibody response (FIG. 3). The Gag-specific antibody titer of mice immunized with Gag sequences combined with the complete LAMP sequence in the p43 vector were markedly greater than those of any of the other immunogens, with a titer of ~300,000 in repeated experiments. Moreover, the titer of the anti-Gag response was maximal at two immunizations. The pcDNA3.I plasmid containing Gag sequences in the complete LAMP sequence also elicited a significant, but much lower titer. The remaining plasmids, including the pcDNA3.1 GagΔINS, showed little immunogenicity in this experiment.

Additional experiments with the secreted LAMP/Gag construct lacking the transmembrane and cytoplasmic domains, and a plasma membrane LAMP/Gag construct lacking the YQTI lysosomal targeting sequence demonstrated that the enhanced antibody response of the LAMP/Gag DNA required lysosomal trafficking. Thus, high protein expression of a secreted Gag failed to elicit a response comparable to the LAMP trafficked Gag, despite the expectation that a secreted Gag would favor an antibody response. Additionally, here was no greater antibody response by co-injecting DNA encoding LAMP/Gag and Gag wild type proteins, implying that additional Gag protein not trafficked to lysosomes had no effect in the antibody response and that the limiting element in this immunization was the $CD4^+$ T-helper response.

Assays of CD4-mediated IL-2 and IL-4 mRNA expression, and IFN-γ protein production, upon stimulation of spleen cells with the p55 Gag recombinant protein all show a much stronger response to immunization with the LAMP/Gag plasmid than with plasmids lacking the complete LAMP (FIGS. 7A-D). While this difference could be attributed to the lack of Gag protein expression in the case of immunization with Gag wild type DNA, the LAMP/secreted Gag was also inferior as an immunogen. The results were specific to $CD4^+$ cells as IFN-γ production was not inhibited by prior incubation of splenocytes with an anti-CD8 monoclonal antibody, whereas it was completely blocked by treatment of the cells by an anti-CD4 antibody. Combined immunization with Gag wild type and LAMP/Gag did not lead to an increased CD4 response.

DNA vaccines are able to generate $CD8^+$ T-cell responses but maximal priming of naïve $CD8^+$ cells requires $CD4^+$ activity. Gag-specific $CD8^+$-mediated responses to a single immunization of 50 μg DNA were measured by in vivo expansion with recombinant vaccinia-Gag-Pol (rVVGag-Pol) for 5 days and activation by the immuno-dominant H2 Kd-restricted Gag peptide for 2 hrs. Mice immunized with LAMP/gag DNA uniformly showed a markedly greater $CD8^+$ response than did those immunized with wild type gag or the secreted LAMP/Gag chimera. The results were comparable with each of three assays, Gag tetramer binding, intra-cellular IFN-γ staining, and Gag-specific cell killing. Removal of $CD8^+$ cells from the effector population abolished the effect. Co-immunization with a plasmid encoding wild type Gag in order to increase Gag protein delivered to the MHC I pathway of transfected cells did not enhance the $CD8^+$-mediated responses, indicating that despite LAMP targeting of antigen there was sufficient MHC I presentation of antigen.

Dose-response to immunization with pITR/LAMP/Gag. Mice twice immunized i.m. with 0.1 to 50 mg of LAMP/gag DNA showed a comparable response to 10 and 50 mg in assays of Gag-specific antibody response, $CD4^+$ INF-γ production, and the % INF-γ$^+$, $CD8^+$ T cells. Cellular responses appeared to require smaller amounts of DNA, with maximum $CD4^+$ and $CD8^+$ responses with 10 mg DNA and a significant $CD8^+$ response with only 1 mg. Others have reported that higher doses of immunogen are necessary to induce humoral immunity as compared to cellular responses.

Example 3

Further Evaluation of the Immune Response of Mice to HIV-1 Gag Encoded as a Full Length Lamp Chimera in the p43 Plasmid Vector; a Repeat Study and Additional Controls Groups of 6 mice were immunized with 50 μg of DNA at the base of the tail on days 0 and 30 with the plasmid constructs as below. Blood samples were obtained on days-1, 29, and 45, and half of the mice sacrificed on day 45. The primary goal of this experiment, was to confirm the initial result of the p43(AAV-ITR) LAMP/Gag/TMCD plasmid and to include additional control immunizations. A number of different constructs were evaluated: 1) p43 (AAV-ITR) (plasmid negative control); 2) p43 (AAV-ITR) LAMP (LAMP negative control without gag); 3) p43 (AAV-ITR) wild type Gag; 4) p43 (AAV-ITR) lumenal domain of LAMP/Gag/LAMP transmembrane and cytoplasmic domains; 5) pVax wild type Gag; and 6) pVax lumenal domain of LAMP/Gag/LAMP transmembrane and cytoplasmic domains.

The anti-HIV specific antibody response at day 29 after the first immunization and 15 days after the second immunization; is given as the average of the results from individual mice at a 1.300 dilution of the plasma sample (n=6) (FIG. 4A). The data again show that the predominant response was after the second immunization of mice innoculated with the p43 (AAV-ITR) lumenal domain of LAMP/Gag/LAMP transmembrand and cytoplasmic domains. This positive response can be attributed to two factors: the increased protein expression of Gag by the p43 plasmid with the Gag gene inserted into the LAMP sequences, and the LAMP trafficking of the protein.

The titer of total IgG. IgG1 and IgG2a were determined. The mice innoculated with the p43 (AAV-ITR) lumenal domain of LAMP/Gag/LAMP transmembrand and cytoplasmic domains presented a titer of total IgG and IgG1 of 1:24, 300 whereas the Gag WT presented a titer of 1:900 (FIG. 6, A). In addition, the p43 (AAV-ITR) lumenal domain of LAMP/Gag/LAMP transmembrane and cytoplasmic domains presented a titer of IgG2a of 1:300 while the Gag WT did not show any IgG2a.

The Gag specific T cell interleukin-4 and INF gamma response of mice immunized as described in FIG. 5, was measured at day 45 by real time PCR assay (FIGS. 7 and 8). Spleen cells were stimulated overnight by medium (control), and medium containing 5 μg Gag protein. A strong Gag-specific response of cells from the p43 LAMP/Gag plasmid immunized mice was observed, indicative of the stimulation of Th2 cells. Together, the T cell production of both INFγ and IL-4 suggests a balanced T cell response to the immunization.

Example 4

Cell C-Type Lectin Receptor/Gag DNA Chimera Targeting to MHC II (LAMP/Gag/DCLR)

Dendritic cell C-type lectin receptors (DCLR) internalize bound antigens by adsorptive endocytosis and traffic to the MHC II compartment where they co-localized with both the multicellular and DC-LAMP molecules. The DCLR may also act in controlling the character of the immune response. Studies of the DEC-205 (DEC) transmembrane and cytoplasmic sequences as signals for the trafficking of a chimera LAMP/p55Gag/DCLR protein were performed. The LAMP lumenal domain sequences are retained in this construct in order to enhance Gag protein expression. The preliminary data show that cells transfected with the LAMP/Gag/DCLR construct express high levels of the Gag protein, that Gag is colocalized with LAMP and MHC II in the transfected cells, and that immunized mice elicit an effective antibody and strong $CD4^+$ responses, but possibly limited $CD8^+$ T cell responses.

Plasmid Constructs

RNA from C57BL/6 mouse bone marrow cells was used as template for cloning the transmembrane domain and cytoplasmic 31 amino acid tail of DEC205 as a model DCLR system. These DEC domains were then used to replace the corresponding LAMP transmembrane fragment and cytosolic 11 amino acid tail of the LAMP/Gag construct in the pITR vector backbone. The membrane-proximal coated pit and distal EDE sequences of DEC205 are believed to play roles in DEC205 recycling between plasma membrane and late endosome/lysosome compartment (Mahnke, et al, 2000).

The following combinations of this sequence were synthesized in the AAV-ITR-containing vector backbone (PITR) (FIG. 8): mLAMP/DEC (negative control, without antigen); p55Gag (wild type HIV-1 Gag); mLAMP/p55Gag (multicellular mLAMP/p55Gag construct as a positive control); mLAMP/p55Gag/DEC (experimental construct); LAMP/p55Gag/DEC $_7$(control construct terminated at amino acid 7 of the cytoplasmic domain of DEC, thus lacking the MHC II targeting sequences).

LAMP/Gag/DCLR Chimera Protein Expression

Expression of Gag was analyzed with transfected COS-7 cells (FIG. 9). As expected, there was detectable wild type Gag expressed by the pITR/gag plasmid (lane 2), and greatly enhanced levels of the LAMP/Gag/DCLR (lane 3 & 4) and LAMP/Gag (lane 5) protein chimeras. This over exposed gel also reveals many degraded fragments of the LAMP/Gag chimeras reacting with the anti-Gag antibody.

Cellular Trafficking of Protein Chimeras Containing the DEC DCLR Cytoplasmic Domain.

The cellular localization of LAMP/DCLR and LAMP/Gag/DCLR chimeras in transfected human 293 cells have been examined by immunofluorescence microscopy. As expected, the mLAMP/DCLR chimera lacking the lysosomal targeting signal (stained with anti-mouse LAMP) was found at the plasma membrane, in contrast to the lysosomal localization of the endogenous human LAMP (stained with anti-human LAMP) (FIGS. 10A-F). However, and surprisingly, the mLAMP/Gag/DCLR chimera, was located in intracellular vesicles, partially colocalized with the endogenous LAMP of the human cell.

Immune Responses of Mice Inoculated with the LAMP/Gag/DCLR DNA Chimera

BALB/c mice (n=8) are immunized intramuscularly with 50 μg DNA (prime) followed in 3 weeks with 10 μg DNA (boost). The antibody titer of samples taken 2 weeks after the boost injection showed a high titer response to the LAMP/Gag/DCLR construct versus the absence of detectable response to wild type Gag encoded by the Gag DNA construct (FIGS. 11A, B, C1-C3). CD4+ mediated responses measured by IL-4 mRNA synthesis and ELISA assay of IFN-γ production were comparable to the high level response to the standard LAMP/Gag construct. In contrast, the $CD8^+$ responses to LAMP/Gag/DCLR, assayed by Gag-specific tetramer binding and intracellular IFN-γ staining, were consistently less than those elicited by LAMP/Gag. This difference of low $CD8^+$ and high $CD4^+$ and antibody responses is subject to further investigation. There possibly is a Th2 bias in the immune response to this DCLR chimera vaccine construct.

Example 6

AAV Vector Constructs

The following AAV vector DNA vaccine constructs were synthesized: AAV/LAMP (negative control); AAV/Gag (wild type Gag); AAV/LAMP/Gag (LAMP/Gag chimera); AAV/hDC-LAMP/Gag (hDC-LAMP/Gag chimera); AAV/LAMP/Gag/DCLR (LAMP/Gag/DCLR chimera).

Immunization Protocol, Initial Experiments

Two initial immunization studies have been performed under conditions of our conventional protocol: DNA prime, 50 μg IM at day 1, followed by DNA boost, 10 μg IM, or AAV boost, $5 \times 10^9$ genomic copies, at day 21. Animals were also immunized only once with the AAV vector. Animals were sacrificed at day 31 for $CD8^+$ response assays, at day 39-40 for $CD4^+$ response assays, and at day 90 for $CD4^+$ and $CD8^+$ assays. Bleedings were taken before immunization and at 3-4 week intervals throughout the experiment for antibody assays, and were continued at monthly intervals for 6 months to date with the remaining mice. Two independent mouse immunization experiments have been initiated to date; one is at 6 months duration and the other at 2 months.

Immune Response of Mice & Duration of Immunity, Initial Experiments

Cellular Immune Responses:

In general, under conditions of this protocol and with the assay time points as above, comparing naked DNA and the AAV vector as the boost immunization, there was no clear advantage of the AAV boost as compared to the naked DNA boost, up to day 90.

Antibody Responses

In keeping with the literature on the AAV vector system, it appears that one obvious difference to naked DNA is a sustained humoral response, presumably due to long-term expression of the antigen (Table 1). As observed in our previous experiments, inoculation with the LAMP/gag chimera elicited a rapid Gag specific IgG response, with a titer in this experiment of 72,000 two weeks after the boost immunization. Without additional immunizations this IgG response rapidly diminished to virtual background levels 3-4 months later. In contrast, immunization with the AAV vector resulted in a slower onset, but a sustained and much higher titer IgG response. Notably, after DNA prime, the AAV/LAMP/Gag/DCLR chimera, with a single AAV boost, resulted in a sustained IgG titer of over 200,000, approximately 10-fold greater than the response to the AAV/LAMP/Gag construct. These data further suggest a Th2 bias of the DCLR system.

TABLE 1

HIV-1 Antibody Titers From Pooled Serum Of Immunized Mice*
[This table did not reproduce]

| Vaccine | Day | | | | |
|---|---|---|---|---|---|
| | 11 | 34 | 68 | 91 | 133 |
| AAV WT | — | — | — | — | — |
| LAMP/Gag (DNA/DNA) | — | 72,000 | 900 | 300 | — |
| LAMP/Gag (DNA/AAV) | — | 2,700 | 8,100 | 24,000 | 24,000 |
| LAMP/Gag (AAV) | — | 8,100 | 2,700 | 2,700 | 2,700 |
| LAMP/Gag/DCLR (DNA/AAV) | — | 24,000 | >218,000 | >218,000 | 218,000 |
| LAMP/Gag/DCLR (AAV) | — | 2,700 | 8,100 | 8,100 | 24,000 |

*The inoculation protocol is indicated in the parenthesis, i.e., (DNA/DNA) indicates 2

Variations, modifications, and other implementations of what is described herein will occur to those of ordinary skill in the art without departing from the spirit and scope of the invention and the claims.

All of the patents, patent applications, international applications, and references identified are expressly incorporated herein by reference in their entireties.

The invention claimed is:

1. A chimeric protein comprising: (1) an antigen domain comprising at least one epitope inserted between (2) a trafficking domain and (3) a transmembrane domain of a lysosomal membrane polypeptide, wherein the trafficking domain is the luminal domain of a lysosomal membrane polypeptide and directs both membrane and non-membrane proteins to an endosomal/lysosomal compartment in a cell or to a lysosome-related organelle.

2. The chimeric protein according to claim 1, wherein the lysosomal membrane polypeptide comprises lysosome associated membrane protein (LAMP)-1, LAMP-2, LAMP-3, DC-LAMP, or LIMP polypeptide.

3. The chimeric protein according to claim 1, wherein the protein further comprises one or more domains selected from the group consisting of: a targeting domain for targeting a protein to a endosomal/lysosomal compartment or lysosome-related organelle; a signal domain; a di-leucine domain; a Tyr motif domain; a proline rich domain; and a Ser-Val-Val domain.

4. The chimeric protein according to claim 3, wherein the Tyr motif domain comprises the tetrapeptide sequence Tyr-Xaa-Xaa-Xbb, wherein Xaa is any amino acid and Xbb is a hydrophobic amino acid.

5. The chimeric protein according to claim 1, wherein the compartment or organelle comprises MHC class II molecules.

6. The chimeric protein according to claim 1, wherein trafficking to the compartment and/or organelle results in processing of the antigen.

7. The chimeric protein according to claim 6, wherein the processed antigen is expressed on the surface of a cell bound to an MHC class II molecule.

8. The chimeric protein according to claim 1, wherein the antigen is selected from the group consisting of: a portion of an antigenic material from a pathogenic organism.

9. The chimeric protein according to claim 8, wherein the pathogenic organism is a virus, microorganism, or parasite.

10. The chimeric protein according to claim 9, wherein the virus is an HIV virus.

11. The chimeric protein according to claim 1, wherein the endosomal compartment is selected from the group consisting of: MIIC, CIIV, melanosomes, secretory granule, lytic granule, platelet-dense granule, basophil granule, Birbeck granule, phagolysosome, and secretory lysosome.

12. The chimeric protein according to claim 1, wherein the chimeric protein elicits an antigen-specific immune response.

13. The chimeric protein according to claim 1 wherein said compartment or organelle comprises a LAMP polypeptide.

* * * * *